(12) United States Patent
Shelton, IV

(10) Patent No.: US 11,304,702 B2
(45) Date of Patent: Apr. 19, 2022

(54) SURGICAL CLIP HAVING COMPLIANT PORTION

(71) Applicant: Ethicon LLC, Guaynabo, PR (US)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 44 days.

(21) Appl. No.: 16/784,330

(22) Filed: Feb. 7, 2020

(65) Prior Publication Data

US 2020/0246012 A1 Aug. 6, 2020

Related U.S. Application Data

(63) Continuation of application No. 15/483,419, filed on Apr. 10, 2017, now abandoned, which is a (Continued)

(51) Int. Cl.
*A61B 17/122* (2006.01)
*A61B 17/00* (2006.01)

(52) U.S. Cl.
CPC .. *A61B 17/122* (2013.01); *A61B 2017/00004* (2013.01); *A61B 2017/00862* (2013.01); *A61B 2017/00946* (2013.01)

(58) Field of Classification Search
CPC . A61B 17/122; A61B 17/1227; A61B 17/128; A61B 17/064; A61B 17/08; A61B 17/12; A61B 17/083; A61B 17/0487; A61B 17/0682; A61B 17/28; A61B 17/282; A61B 2017/2825; A61B 2017/00004; A61B 2017/00862; A61B 2017/00858; A61B 2017/00893; A61B 2017/00946; A61B 2017/2808; A61B 2017/00668; A61B 2017/0618; A61L 31/14; A61L 15/60

See application file for complete search history.

(56) References Cited

U.S. PATENT DOCUMENTS 1,306,107 A 6/1919 Elliott
2,132,295 A 10/1938 Hawkins
(Continued)

FOREIGN PATENT DOCUMENTS

CN 1634601 A 7/2005
DE 273689 C1 5/1914
(Continued)

OTHER PUBLICATIONS

B.R. Coolman, Dvm, Ms, et al., Comparison of Skin Staples With Sutures for Anastomosis of the Small Intestine in Dogs:Abstract, Online: http://www3.intersclence.wiley.com/journal/119040681/abstract?CRETRY=1&SRETRY=0, Accessed: Sep. 22, 2008, 2 Pages.

(Continued)

*Primary Examiner* — Mohamed G Gabr

(57) ABSTRACT

A clip is provided that can be used for ligating tissue, such as vessels, other tubular ducts, and the like. The clip has opposed first and second leg members having proximal and distal ends. The proximal end of each leg member is connected by an apex. The clip has a compliant portion formed on the inner surface of at least one of the first and second leg members. The compliant portion can fill gaps left by springback of the clip after formation.

13 Claims, 13 Drawing Sheets

Related U.S. Application Data continuation of application No. 15/045,284, filed on Feb. 17, 2016, now abandoned, which is a continuation of application No. 14/025,904, filed on Sep. 13, 2013, now abandoned.

(56) References Cited

U.S. PATENT DOCUMENTS

| | | |
|---|---|---|
| 2,161,632 A | 5/1939 | Nattenheimer |
| 2,221,111 A | 8/1940 | Hess |
| 2,526,902 A | 10/1950 | Rublee |
| 2,674,149 A | 4/1954 | Benson |
| 2,853,074 A | 9/1958 | Olson |
| 3,006,344 A | 10/1961 | Vogelfanger |
| 3,032,769 A | 5/1962 | Palmer |
| 3,120,230 A | 2/1964 | Skold |
| 3,166,072 A | 1/1965 | Sullivan |
| 3,357,296 A | 12/1967 | Lefever |
| 3,363,628 A | 1/1968 | Wood |
| 3,490,675 A | 1/1970 | Green et al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,744,495 A | 7/1973 | Johnson |
| 3,746,002 A | 7/1973 | Haller |
| 3,819,100 A | 6/1974 | Noiles et al. |
| 3,841,474 A | 10/1974 | Maier |
| 3,867,944 A | 2/1975 | Samuels |
| 3,885,491 A | 5/1975 | Curtis |
| RE28,932 E | 8/1976 | Noiles et al. |
| 4,060,089 A | 11/1977 | Noiles |
| 4,188,953 A | 2/1980 | Klieman et al. |
| 4,275,813 A | 6/1981 | Noiles |
| 4,305,539 A | 12/1981 | Korolkov et al. |
| 4,321,002 A | 3/1982 | Froehlich |
| 4,331,277 A | 5/1982 | Green |
| 4,340,331 A | 7/1982 | Savino |
| 43,794,571 | 4/1983 | Gravener et al. |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,434,796 A | 3/1984 | Karapetian et al. |
| 4,438,659 A | 3/1984 | Desplats |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,530,453 A | 7/1985 | Green |
| 4,548,202 A | 10/1985 | Duncan |
| 4,566,620 A | 1/1986 | Green et al. |
| 4,573,622 A | 3/1986 | Green et al. |
| 4,580,712 A | 4/1986 | Green |
| 4,589,416 A | 5/1986 | Green |
| 4,605,001 A | 8/1986 | Rothfuss et al. |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,634,419 A | 1/1987 | Kreizman et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,719,917 A | 1/1988 | Barrows et al. |
| 4,728,020 A | 3/1988 | Green et al. |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,834,720 A | 5/1989 | Blinkhorn |
| 4,844,066 A | 7/1989 | Stein |
| 4,844,068 A | 7/1989 | Arata et al. |
| 4,865,030 A | 9/1989 | Polyak |
| 4,869,414 A | 9/1989 | Green et al. |
| 4,869,415 A | 9/1989 | Fox |
| 4,890,613 A | 1/1990 | Golden et al. |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,976,722 A | 12/1990 | Failla |
| 4,978,333 A | 12/1990 | Broadwin et al. |
| 4,986,808 A | 1/1991 | Broadwin et al. |
| 5,002,553 A | 3/1991 | Shiber |
| 5,015,227 A | 5/1991 | Broadwin et al. |
| 5,038,109 A | 8/1991 | Goble et al. |
| 5,065,929 A | 11/1991 | Schulze et al. |
| 5,071,430 A | 12/1991 | de Salis et al. |
| 5,074,454 A | 12/1991 | Peters |
| 5,088,997 A | 2/1992 | Delahuerga et al. |
| 5,104,397 A | 4/1992 | Vaconcelos et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,156,614 A | 10/1992 | Green et al. |
| 5,158,567 A | 10/1992 | Green |
| D330,699 S | 11/1992 | Gill |
| 5,171,253 A * | 12/1992 | Klieman .............. A61B 17/122 |
| | | 128/DIG. 15 |
| 5,190,517 A | 3/1993 | Zieve et al. |
| 5,201,746 A | 4/1993 | Shichman |
| 5,211,649 A | 5/1993 | Kohler et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,258,009 A | 11/1993 | Conners |
| 5,258,012 A | 11/1993 | Luscombe et al. |
| 5,263,973 A | 11/1993 | Cook |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,304,204 A | 4/1994 | Bregen |
| 5,312,023 A | 5/1994 | Green et al. |
| 5,312,329 A | 5/1994 | Beaty et al. |
| 5,336,232 A | 8/1994 | Green et al. |
| 5,342,395 A | 8/1994 | Jarrett et al. |
| 5,342,396 A | 8/1994 | Cook |
| 5,346,504 A | 9/1994 | Ortiz et al. |
| 5,350,400 A | 9/1994 | Esposito et al. |
| 5,352,229 A | 10/1994 | Goble et al. |
| 5,352,238 A | 10/1994 | Green et al. |
| 5,358,506 A | 10/1994 | Green et al. |
| 5,358,510 A | 10/1994 | Luscombe et al. |
| 5,364,001 A | 11/1994 | Bryan |
| 5,366,479 A | 11/1994 | McGarry et al. |
| 5,370,645 A | 12/1994 | Klicek et al. |
| 5,372,596 A | 12/1994 | Klicek et al. |
| 5,382,247 A | 1/1995 | Cimino et al. |
| 5,383,880 A | 1/1995 | Hooven |

(56) References Cited

U.S. PATENT DOCUMENTS

| | | |
|---|---|---|
| 5,395,033 A | 3/1995 | Byrne et al. |
| 5,395,384 A | 3/1995 | Duthoit |
| 5,397,324 A | 3/1995 | Carroll et al. |
| 5,405,072 A | 4/1995 | Zlock et al. |
| 5,405,344 A | 4/1995 | Williamson et al. |
| 5,411,508 A | 5/1995 | Bessler et al. |
| 5,413,272 A | 5/1995 | Green et al. |
| 5,415,334 A | 5/1995 | Williamson, IV et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,433,721 A | 7/1995 | Hooven et al. |
| 5,438,302 A | 8/1995 | Goble |
| 5,441,191 A | 8/1995 | Linden |
| 5,441,193 A | 8/1995 | Gravener |
| 5,441,483 A | 8/1995 | Avitall |
| 5,445,644 A | 8/1995 | Pietrafitta et al. |
| 5,447,417 A | 9/1995 | Kuhl et al. |
| 5,452,837 A | 9/1995 | Williamson, IV et al. |
| 5,462,215 A | 10/1995 | Viola et al. |
| 5,466,020 A | 11/1995 | Page et al. |
| 5,468,253 A | 11/1995 | Bezwada et al. |
| 5,472,442 A | 12/1995 | Klicek |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,509,920 A | 4/1996 | Phillips et al. |
| 5,520,678 A | 5/1996 | Heckele et al. |
| 5,520,700 A | 5/1996 | Beyar et al. |
| 5,541,376 A | 7/1996 | Ladtkow et al. |
| 5,549,621 A | 8/1996 | Bessler et al. |
| 5,560,530 A | 10/1996 | Bolanos et al. |
| 5,571,285 A | 11/1996 | Chow et al. |
| 5,575,803 A | 11/1996 | Cooper et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,599,344 A | 2/1997 | Paterson |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,611,709 A | 3/1997 | McAnulty |
| 5,613,966 A | 3/1997 | Makower et al. |
| 5,619,992 A | 4/1997 | Guthrie et al. |
| 5,624,452 A | 4/1997 | Yates |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,683,349 A | 11/1997 | Makower et al. |
| 5,685,474 A | 11/1997 | Seeber |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Bolarski et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdortf |
| 5,697,943 A | 12/1997 | Sauer et al. |
| 5,702,387 A | 12/1997 | Arts et al. |
| 5,702,408 A | 12/1997 | Wales et al. |
| 5,702,409 A | 12/1997 | Rayburn et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,718,548 A | 2/1998 | Costellessa |
| 5,720,744 A | 2/1998 | Eggleston et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,733,308 A | 3/1998 | Daugherty et al. |
| 5,735,874 A | 4/1998 | Measamer et al. |
| 5,738,474 A | 4/1998 | Blewett |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,766,188 A | 6/1998 | Igaki |
| 5,772,379 A | 6/1998 | Evensen |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,799,857 A | 9/1998 | Robertson et al. |
| 5,800,379 A | 9/1998 | Edwards |

(56) References Cited

U.S. PATENT DOCUMENTS

| | | | |
|---|---|---|---|
| 5,806,676 A | 9/1998 | Wasgien |
| 5,807,393 A | 9/1998 | Williamson, IV et al. |
| 5,810,855 A | 9/1998 | Rayburn et al. |
| 5,814,055 A | 9/1998 | Knodel et al. |
| 5,814,057 A | 9/1998 | Oi et al. |
| 5,820,009 A | 10/1998 | Melling et al. |
| 5,826,776 A | 10/1998 | Schulze et al. |
| 5,827,271 A | 10/1998 | Buysse et al. |
| 5,829,662 A | 11/1998 | Allen et al. |
| 5,833,695 A | 11/1998 | Yoon |
| 5,836,503 A | 11/1998 | Ehrensfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,101 A | 12/1998 | Fry |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,894,979 A | 4/1999 | Powell |
| 5,897,552 A | 4/1999 | Edwards et al. |
| 5,897,562 A | 4/1999 | Bolanos et al. |
| 5,901,895 A | 5/1999 | Heaton et al. |
| 5,902,312 A | 5/1999 | Frater |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,937,951 A | 8/1999 | Izuchukwu et al. |
| 5,941,442 A | 8/1999 | Geiste et al. |
| 5,944,715 A | 8/1999 | Goble et al. |
| 5,947,984 A | 9/1999 | Whipple |
| 5,951,552 A | 9/1999 | Long et al. |
| 5,954,259 A | 9/1999 | Viola et al. |
| 5,964,774 A | 10/1999 | McKean et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,024,748 A | 2/2000 | Manzo et al. |
| 6,027,501 A | 2/2000 | Goble et al. |
| 6,032,849 A | 3/2000 | Mastri et al. |
| 6,033,399 A | 3/2000 | Gines |
| 6,039,734 A | 3/2000 | Goble |
| 6,045,560 A | 4/2000 | McKean et al. |
| 6,050,996 A | 4/2000 | Schmaltz et al. |
| 6,053,390 A | 4/2000 | Green et al. |
| 6,053,922 A | 4/2000 | Krause et al. |
| 6,063,097 A | 5/2000 | Oi et al. |
| 6,068,627 A | 5/2000 | Orszulak et al. |
| 6,074,401 A | 6/2000 | Gardiner et al. |
| 6,083,191 A | 7/2000 | Rose |
| 6,083,234 A | 7/2000 | Nicholas et al. |
| 6,083,242 A | 7/2000 | Cook |
| 6,086,600 A | 7/2000 | Kortenbach |
| 6,093,186 A | 7/2000 | Goble |
| 6,099,551 A | 8/2000 | Gabbay |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,139,547 A | 10/2000 | Lontine et al. |
| 6,149,660 A | 11/2000 | Laufer et al. |
| 6,156,056 A | 12/2000 | Kearns et al. |
| 6,162,208 A | 12/2000 | Hipps |
| 6,171,330 B1 | 1/2001 | Benchetrit |
| 6,187,003 B1 | 2/2001 | Buysse et al. |
| 6,193,129 B1 | 2/2001 | Bittner et al. |
| 6,202,914 B1 | 3/2001 | Geiste et al. |
| 6,210,403 B1 | 4/2001 | Klicek |
| 6,213,999 B1 | 4/2001 | Platt, Jr. et al. |
| 6,228,081 B1 | 5/2001 | Goble |
| 6,228,083 B1 | 5/2001 | Lands et al. |
| 6,241,139 B1 | 6/2001 | Milliman et al. |
| 6,250,532 B1 | 6/2001 | Green et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,302,311 B1 | 10/2001 | Adams et al. |
| 6,315,184 B1 | 11/2001 | Whitman |
| 6,322,494 B1 | 11/2001 | Bullivant et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,334,861 B1 | 1/2002 | Chandler et al. |
| 6,336,926 B1 | 1/2002 | Goble |
| 6,358,224 B1 | 3/2002 | Tims et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,797 B2 | 6/2002 | Bombard et al. |
| 6,402,766 B2 | 6/2002 | Bowman et al. |
| 6,416,509 B1 | 7/2002 | Goble et al. |
| RE37,814 E | 8/2002 | Allgeyer |
| 6,436,107 B1 | 8/2002 | Wang et al. |
| 6,436,110 B2 | 8/2002 | Bowman et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,551,333 B2 | 4/2003 | Kuhns et al. |
| 6,558,379 B1 | 5/2003 | Batchelor et al. |
| 6,569,085 B2 | 5/2003 | Kortenbach et al. |
| 6,578,751 B2 | 6/2003 | Hartwick |
| 6,579,304 B1 * | 6/2003 | Hart ................. A61B 17/02 606/157 |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,602,252 B2 | 8/2003 | Mollenauer |
| 6,607,475 B2 | 8/2003 | Doyle et al. |
| 6,616,686 B2 | 9/2003 | Coleman et al. |
| 6,619,529 B2 | 9/2003 | Green et al. |
| 6,626,922 B1 | 9/2003 | Hart et al. |
| 6,629,630 B2 | 10/2003 | Adams |
| 6,629,988 B2 | 10/2003 | Weadock |
| 6,638,285 B2 | 10/2003 | Gabbay |
| 6,644,532 B2 | 11/2003 | Green et al. |
| 6,656,193 B2 | 12/2003 | Grant et al. |
| 6,671,185 B2 | 12/2003 | Duval |
| 6,681,978 B2 | 1/2004 | Geiste et al. |
| 6,681,979 B2 | 1/2004 | Whitman |
| 6,692,507 B2 | 2/2004 | Pugsley et al. |
| 6,695,199 B2 | 2/2004 | Whitman |
| 6,698,643 B2 | 3/2004 | Whitman |
| 6,716,232 B1 | 4/2004 | Vidal et al. |
| 6,716,233 B1 | 4/2004 | Whitman |
| 6,722,552 B2 | 4/2004 | Fenton, Jr. |
| 6,726,697 B2 | 4/2004 | Nicholas et al. |
| 6,736,854 B2 | 5/2004 | Vadurro et al. |
| 6,747,121 B2 | 6/2004 | Gogolewski |
| 6,749,560 B1 | 6/2004 | Konstorum et al. |
| 6,755,338 B2 | 6/2004 | Hahnen et al. |
| 6,761,685 B2 | 7/2004 | Adams et al. |
| 6,769,594 B2 | 8/2004 | Orban, III |
| 6,773,437 B2 | 8/2004 | Ogilvie et al. |

(56) References Cited

U.S. PATENT DOCUMENTS

| | | |
|---|---|---|
| 6,773,438 B1 | 8/2004 | Knodel et al. |
| 6,786,382 B1 | 9/2004 | Hoffman et al. |
| 6,793,652 B1 | 9/2004 | Whitman et al. |
| 6,793,661 B2 | 9/2004 | Hamilton et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,821,284 B2 | 11/2004 | Sturtz et al. |
| 6,830,174 B2 | 12/2004 | Hillstead et al. |
| 6,837,846 B2 | 1/2005 | Jaffe et al. |
| 6,843,403 B2 | 1/2005 | Whitman |
| 6,858,005 B2 | 2/2005 | Ohline et al. |
| RE38,708 E | 3/2005 | Bolanos et al. |
| 6,863,694 B1 | 3/2005 | Boyce et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,877,647 B2 | 4/2005 | Ratcliff et al. |
| 6,878,106 B1 | 4/2005 | Herrmann |
| 6,905,057 B2 | 6/2005 | Swayze et al. |
| 6,913,608 B2 | 7/2005 | Liddicoat et al. |
| 6,932,810 B2 | 8/2005 | Ryan |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,978,921 B2 | 12/2005 | Shelton, IV et al. |
| 6,978,922 B2 | 12/2005 | Biotti et al. |
| 6,981,628 B2 | 1/2006 | Wales et al. |
| 6,981,978 B2 | 1/2006 | Gannoe |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,651 B2 | 1/2006 | Stevenson et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,052,494 B2 | 5/2006 | Goble et al. |
| 7,055,731 B2 | 6/2006 | Shelton, IV et al. |
| 7,056,330 B2 | 6/2006 | Gayton |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,637 B2 | 8/2006 | Danitz et al. |
| 7,090,684 B2 | 8/2006 | McGuckin, Jr. et al. |
| 7,094,247 B2 | 8/2006 | Monassevitch et al. |
| 7,097,644 B2 | 8/2006 | Long |
| 7,104,741 B2 | 9/2006 | Krohn |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,137,981 B2 | 11/2006 | Long |
| 7,140,527 B2 | 11/2006 | Ehrenfels et al. |
| 7,143,923 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,182,239 B1 | 2/2007 | Myers |
| 7,188,758 B2 | 3/2007 | Viola et al. |
| 7,199,537 B2 | 4/2007 | Okamura et al. |
| 7,204,835 B2 | 4/2007 | Latterell et al. |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,210,609 B2 | 5/2007 | Leiboff et al. |
| 7,211,081 B2 | 5/2007 | Goble |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,282,048 B2 | 10/2007 | Goble et al. |
| 7,296,722 B2 | 11/2007 | Ivanko |
| 7,296,724 B2 | 11/2007 | Green et al. |
| 7,300,450 B2 | 11/2007 | Vieugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,203 B2 | 2/2008 | Papineau et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,336,048 B2 | 2/2008 | Lohr |
| 7,341,591 B2 | 3/2008 | Grinberg |
| 7,354,447 B2 | 4/2008 | Shelton, IV et al. |
| 7,357,806 B2 | 4/2008 | Rivera et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |

(56) References Cited

U.S. PATENT DOCUMENTS

| | | |
|---|---|---|
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,517,356 B2 | 4/2009 | Heinrich |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,453 B2 | 7/2009 | Heinrich et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,637,409 B2 | 12/2009 | Marczyk et al. |
| 7,638,958 B2 | 12/2009 | Philipp et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,848 B2 | 1/2010 | Swayze et al. |
| 7,645,230 B2 | 1/2010 | Mikkaichi et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,682,307 B2 | 3/2010 | Danitz et al. |
| 7,699,204 B2 | 4/2010 | Viola |
| 7,699,846 B2 | 4/2010 | Ryan |
| 7,699,856 B2 | 4/2010 | Van Wyk et al. |
| 7,708,180 B2 | 5/2010 | Murray et al. |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,731,724 B2 | 6/2010 | Huitema et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,744,628 B2 | 6/2010 | Viola |
| 7,748,587 B2 | 7/2010 | Haramiishi et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,775 B2 | 8/2010 | Shelton, IV et al. |
| 7,776,060 B2 | 8/2010 | Mooradian et al. |
| 7,780,054 B2 | 8/2010 | Wales |
| 7,780,663 B2 | 8/2010 | Yates et al. |
| 7,780,685 B2 | 8/2010 | Hunt et al. |
| 7,784,663 B2 | 8/2010 | Shelton, IV |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Huell et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,426 B2 | 11/2010 | Racenet et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,537 B2 | 12/2010 | Shelton, IV et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,893,586 B2 | 2/2011 | West et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,221 B2 | 3/2011 | Viola |
| 7,913,891 B2 | 3/2011 | Doll et al. |
| 7,914,543 B2 | 3/2011 | Roth et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,934,630 B2 | 5/2011 | Shelton, IV et al. |
| 7,938,307 B2 | 5/2011 | Bettuchi |

(56) References Cited

U.S. PATENT DOCUMENTS

| | | |
|---|---|---|
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,959,050 B2 | 6/2011 | Smith et al. |
| 7,959,051 B2 | 6/2011 | Smith et al. |
| 7,966,799 B2 | 6/2011 | Morgan et al. |
| 7,967,180 B2 | 6/2011 | Scirica |
| 7,967,839 B2 | 6/2011 | Flock et al. |
| 7,980,443 B2 | 7/2011 | Scheib et al. |
| 7,992,757 B2 | 8/2011 | Wheeler et al. |
| 8,002,795 B2 | 8/2011 | Beetel |
| 8,011,550 B2 | 9/2011 | Aranyi et al. |
| 8,011,551 B2 | 9/2011 | Marczyk et al. |
| 8,011,555 B2 | 9/2011 | Tarinelli et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,097,017 B2 | 1/2012 | Viola |
| 8,100,310 B2 | 1/2012 | Zemlok |
| 8,105,350 B2 | 1/2012 | Lee et al. |
| 8,113,410 B2 | 2/2012 | Hall et al. |
| 8,114,100 B2 | 2/2012 | Smith et al. |
| 8,123,103 B2 | 2/2012 | Milliman |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,141,763 B2 | 3/2012 | Milliman |
| 8,152,041 B2 | 4/2012 | Kostrzewski |
| 8,157,145 B2 | 4/2012 | Shelton, Iv et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,138 B2 | 4/2012 | Bettenhausen et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,124 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,236,010 B2 | 8/2012 | Ortiz et al. |
| 8,241,308 B2 | 8/2012 | Kortenbach et al. |
| 8,241,322 B2 | 8/2012 | Whitman et al. |
| 8,245,899 B2 | 8/2012 | Swensgard et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,292,155 B2 | 10/2012 | Shelton, IV et al. |
| 8,308,040 B2 | 11/2012 | Huang et al. |
| 8,313,496 B2 | 11/2012 | Sauer et al. |
| 8,313,509 B2 | 11/2012 | Kostrzewski |
| 8,317,074 B2 | 11/2012 | Ortiz et al. |
| 8,322,589 B2 | 12/2012 | Boudreaux |
| 8,333,313 B2 | 12/2012 | Boudreaux et al. |
| 8,333,764 B2 | 12/2012 | Francischelli et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,372,094 B2 | 2/2013 | Bettuchi et al. |
| 8,393,514 B2 | 3/2013 | Shelton, IV et al. |
| 8,397,971 B2 | 3/2013 | Yates et al. |
| 8,408,439 B2 | 4/2013 | Huang et al. |
| 8,408,442 B2 | 4/2013 | Racenet et al. |
| 8,413,870 B2 | 4/2013 | Pastorelli et al. |
| 8,413,871 B2 | 4/2013 | Net et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,444,036 B2 | 5/2013 | Shelton, IV |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,459,520 B2 | 6/2013 | Giordano et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,512,359 B2 | 8/2013 | Whitman et al. |
| 8,517,239 B2 | 8/2013 | Scheib et al. |
| 8,517,244 B2 | 8/2013 | Shelton, IV et al. |
| 2002/0117534 A1 | 8/2002 | Green et al. |
| 2002/0177863 A1 | 11/2002 | Mandel et al. |
| 2003/0181900 A1 | 9/2003 | Long |
| 2003/0236505 A1 | 12/2003 | Bonadio et al. |
| 2004/0102783 A1 | 5/2004 | Sutterlin, III et al. |
| 2004/0108357 A1 | 6/2004 | Milliman et al. |
| 2004/0147909 A1 | 7/2004 | Johnston et al. |
| 2004/0164123 A1 | 8/2004 | Racenet et al. |
| 2004/0167552 A1 | 8/2004 | Buelna et al. |
| 2004/0167572 A1 | 8/2004 | Roth et al. |
| 2004/0193189 A1 | 9/2004 | Kortenbach et al. |
| 2004/0222268 A1 | 11/2004 | Bilotti et al. |
| 2004/0225186 A1 | 11/2004 | Horne, Jr. et al. |
| 2004/0243151 A1 | 12/2004 | Demmy et al. |
| 2004/0260315 A1 | 12/2004 | Dell et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0090817 A1 | 4/2005 | Phan |
| 2005/0103819 A1 | 5/2005 | Racenet et al. |
| 2005/0119525 A1 | 6/2005 | Takemoto |
| 2005/0131390 A1 | 6/2005 | Heinrich et al. |
| 2005/0143759 A1 | 6/2005 | Kelly |
| 2005/0145675 A1 | 7/2005 | Hartwick et al. |
| 2005/0119669 A1 | 8/2005 | Demmy |

(56) References Cited

U.S. PATENT DOCUMENTS

| | | |
|---|---|---|
| 2005/0177181 A1 | 8/2005 | Kagan et al. |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0263563 A1 | 12/2005 | Racenet et al. |
| 2005/0274768 A1 | 12/2005 | Cummins et al. |
| 2006/0004407 A1 | 1/2006 | Hiles et al. |
| 2006/0020336 A1 | 1/2006 | Liddicoat |
| 2006/0025813 A1 | 2/2006 | Shelton et al. |
| 2006/0049229 A1 | 3/2006 | Milliman et al. |
| 2006/0052825 A1 | 3/2006 | Ransick et al. |
| 2006/0089535 A1 | 4/2006 | Raz et al. |
| 2006/0100643 A1 | 5/2006 | Laufer et al. |
| 2006/0161185 A1 | 7/2006 | Saadat et al. |
| 2006/0173470 A1 | 8/2006 | Oray et al. |
| 2006/0180634 A1 | 8/2006 | Shelton et al. |
| 2006/0235368 A1 | 10/2006 | Oz |
| 2006/0235468 A1 | 10/2006 | Huitema |
| 2006/0271102 A1 | 11/2006 | Bosshand et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027472 A1 | 2/2007 | Hiles et al. |
| 2007/0051375 A1 | 3/2007 | Milliman |
| 2007/0066981 A1 | 3/2007 | Meagher |
| 2007/0073341 A1 | 3/2007 | Smith |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0170225 A1 | 7/2007 | Shelton, IV et al. |
| 2007/0173687 A1 | 7/2007 | Shima et al. |
| 2007/0173866 A1 | 7/2007 | Sorrentino et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0221700 A1 | 9/2007 | Ortiz et al. |
| 2007/0225562 A1 | 9/2007 | Spivey et al. |
| 2007/0239028 A1 | 10/2007 | Houser et al. |
| 2007/0243227 A1 | 10/2007 | Gertner |
| 2007/0246505 A1 | 10/2007 | Pace-Floridia et al. |
| 2007/0260278 A1 | 11/2007 | Wheeler et al. |
| 2007/0270884 A1 | 11/2007 | Smith et al. |
| 2007/0279011 A1 | 12/2007 | Jones et al. |
| 2007/0286892 A1 | 12/2007 | Herzberg et al. |
| 2007/0295780 A1 | 12/2007 | Shelton, IV et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemick et al. |
| 2008/0128469 A1 | 6/2008 | Dalessandro et al. |
| 2008/0132915 A1 | 6/2008 | Buckman et al. |
| 2008/0140115 A1 | 6/2008 | Stopek |
| 2008/0167522 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0200949 A1 | 8/2008 | Hiles et al. |
| 2008/0251569 A1 | 10/2008 | Smith et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0082789 A1 | 3/2009 | Milliman et al. |
| 2009/0088783 A1 | 4/2009 | Kennedy et al. |
| 2009/0090763 A1 | 4/2009 | Zemlok et al. |
| 2009/0099876 A1 | 4/2009 | Whitman |
| 2009/0149871 A9 | 6/2009 | Kagan et al. |
| 2009/0171380 A1 | 7/2009 | Whiting |
| 2009/0187198 A1 | 7/2009 | Weitzner |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0255974 A1 | 10/2009 | Viola |
| 2010/0069942 A1 | 3/2010 | Shelton, IV |
| 2010/0076475 A1 | 3/2010 | Yates et al. |
| 2010/0089970 A1 | 4/2010 | Smith et al. |
| 2010/0133317 A1 | 6/2010 | Shelton, IV et al. |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0193566 A1 | 8/2010 | Scheib et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243709 A1 | 9/2010 | Hess et al. |
| 2010/0258611 A1 | 10/2010 | Smith et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2010/0331862 A1 | 12/2010 | Monassevitch et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0011914 A1 | 1/2011 | Baxter, III et al. |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0060363 A1 | 3/2011 | Hess et al. |
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155787 A1 | 6/2011 | Baxter, III et al. |
| 2011/0163147 A1 | 7/2011 | Laurent et al. |

(56) References Cited

U.S. PATENT DOCUMENTS

| | | |
|---|---|---|
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295290 A1 | 12/2011 | Whitfield |
| 2011/0295291 A1 | 12/2011 | Trivisani |
| 2011/0295295 A1 | 12/2011 | Shelton, IV et al. |
| 2011/0313437 A1 | 12/2011 | Yeh |
| 2012/0022630 A1 | 1/2012 | Wubbeling |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, Iv et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083803 A1 | 4/2012 | Patel et al. |
| 2012/0083833 A1 | 4/2012 | Shelton, IV et al. |
| 2012/0083834 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton, IV et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, Iv et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0037596 A1 | 2/2013 | Bear et al. |
| 2013/0079814 A1 | 3/2013 | Hess et al. |
| 2013/0146642 A1 | 6/2013 | Shelton, IV et al. |
| 2013/0146643 A1 | 6/2013 | Schmid et al. |
| 2013/0172929 A1 | 7/2013 | Hess et al. |

FOREIGN PATENT DOCUMENTS

| | | |
|---|---|---|
| DE | 1775926 A1 | 1/1972 |
| DE | 3036217 A1 | 4/1982 |
| DE | 3210466 A1 | 9/1983 |
| DE | 19851291 A1 | 1/2000 |
| DE | 19924311 A1 | 11/2000 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0594148 A1 | 4/1994 |
| EP | 0770355 A1 | 5/1997 |
| EP | 0878169 A1 | 11/1998 |
| EP | 0879742 A1 | 11/1998 |
| EP | 0923907 A1 | 6/1999 |
| EP | 1034747 A1 | 9/2000 |
| EP | 1034748 A1 | 9/2000 |
| EP | 1053719 A1 | 11/2000 |
| EP | 1055399 A1 | 11/2000 |
| EP | 1055400 A1 | 11/2000 |

(56) References Cited

FOREIGN PATENT DOCUMENTS

| | | |
|---|---|---|
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1284120 A1 | 2/2003 |
| EP | 0869742 B1 | 5/2003 |
| EP | 0996378 B1 | 6/2004 |
| EP | 1407719 A2 | 4/2005 |
| EP | 1547528 A1 | 6/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1082944 B1 | 5/2006 |
| EP | 1253866 B1 | 7/2006 |
| EP | 1285633 B1 | 12/2006 |
| EP | 1767163 A1 | 3/2007 |
| EP | 1599146 B1 | 10/2007 |
| EP | 1330201 B1 | 6/2008 |
| EP | 2090256 A2 | 8/2009 |
| EP | 1769754 B1 | 6/2010 |
| EP | 1627605 B1 | 12/2010 |
| EP | 1374788 B1 | 10/2011 |
| FR | 999646 A | 2/1952 |
| FR | 1112936 A | 3/1956 |
| FR | 2598905 A1 | 11/1987 |
| FR | 2765794 A1 | 1/1999 |
| GB | 2109241 A | 6/1938 |
| GB | 939929 A | 10/1963 |
| GB | 1210522 A | 10/1970 |
| GB | 1217159 A | 12/1970 |
| GB | 1339394 A1 | 12/1973 |
| GB | 2272159 A | 5/1994 |
| GB | 2336214 A | 10/1999 |
| JP | 312126 A2 | 1/1991 |
| JP | 5212039 A2 | 8/1993 |
| JP | 6007357 A2 | 1/1994 |
| JP | 7051273 A2 | 2/1995 |
| JP | 8033641 A2 | 2/1996 |
| JP | 82229050 A2 | 9/1996 |
| JP | 2000033071 A2 | 2/2000 |
| JP | 2000171730 A2 | 6/2000 |
| JP | 2000287987 A2 | 10/2000 |
| JP | 2001514541 A2 | 9/2001 |
| JP | 2002143078 A2 | 5/2002 |
| JP | 2000325303 A2 | 11/2002 |
| JP | 2005131163 A2 | 5/2005 |
| JP | 2005131164 A2 | 5/2005 |
| JP | 2005131173 A2 | 5/2005 |
| JP | 2005131211 A2 | 5/2005 |
| JP | 2005131212 A2 | 5/2005 |
| JP | 2005137423 A2 | 6/2005 |
| JP | 2006281405 A2 | 10/2006 |
| RU | 2008830 C1 | 3/1994 |
| RU | 2187249 C2 | 3/2004 |
| RU | 2225170 C2 | 3/2004 |
| SU | 189517 A | 1/1967 |
| SU | 328636 | 9/1972 |
| SU | 1009439 A3 | 4/1983 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | 9315648 A1 | 8/1993 |
| WO | 9517855 A1 | 7/1995 |
| WO | 9520360 A1 | 8/1995 |
| WO | 9623448 A1 | 8/1996 |
| WO | 9635464 A1 | 11/1996 |
| WO | 9639086 A1 | 12/1996 |
| WO | 9639088 A1 | 12/1996 |
| WO | 9724073 A1 | 7/1997 |
| WO | 9734533 A1 | 9/1997 |
| WO | 9903407 A1 | 1/1999 |
| WO | 9903409 A1 | 1/1999 |
| WO | 0024322 A1 | 5/2000 |
| WO | 0024330 A1 | 5/2000 |
| WO | 0053112 A2 | 9/2000 |
| WO | 0057796 A1 | 10/2000 |
| WO | 0105702 A1 | 1/2001 |
| WO | 0110482 A1 | 2/2001 |
| WO | 0154594 A1 | 8/2001 |
| WO | 0158371 A1 | 8/2001 |
| WO | 0162164 A2 | 8/2001 |
| WO | 0162169 A2 | 8/2001 |
| WO | 0191646 A1 | 12/2001 |
| WO | 0236028 A1 | 5/2002 |
| WO | 0243571 A2 | 6/2002 |
| WO | 03055402 A1 | 7/2003 |
| WO | 2003079909 A3 | 10/2003 |
| WO | 03094747 A1 | 11/2003 |
| WO | 2004047626 A1 | 6/2004 |
| WO | 2004047653 A2 | 6/2004 |
| WO | 2004056277 A1 | 7/2004 |
| WO | 2004078050 A2 | 9/2004 |
| WO | 2004078051 A2 | 9/2004 |
| WO | 2004096015 A2 | 11/2004 |
| WO | 2006044581 A2 | 4/2006 |
| WO | 2006051252 A1 | 5/2006 |
| WO | 2006059067 A1 | 6/2006 |
| WO | 2007137304 A2 | 11/2007 |
| WO | 2007142625 A2 | 12/2007 |
| WO | 2008021969 A2 | 2/2008 |
| WO | 2008089404 A2 | 7/2008 |

OTHER PUBLICATIONS

Biomedical Coatings, Research Products Corporation, Fort Wayne Metals, Jun. 21, 2010, 1 Page, www.fwmetals.com.

Breedveld et al., A New, Easily Miniaturized Steerable Endoscope, IEEE Engineering in Medicine and Biology Magazine, Nov./Dec. 2005, pp. 40-47.

C.C. Thompson et al., Peroral Endoscopic Reduction of Dilated Gastrojejunal Anastomosis After Roux-en-Y Gastric Bypass:, A Possible New Option for Patients with Weight Regain, 2006, vol. 20, pp. 1744-1748, Surg Endosc.

Datasheet for Panasonic TK Relays, Ultra Low Profile 2 A Polarized Relay, Known of at least as early as Aug. 17, 2010, 5 Pages, Matsushita Electric Works, Ltd.

Disclosed Anonymously, Motor-Driven Surgical Stapler Improvements, Research Disclosure Database No. 526041, Published: Feb. 2008, 10 Pages.

Don Tuite, Get The Lowdown On Ultracapacitors, (online) URL: http://electronicdesign.com/Articles/Print.cfm?ArticleID=17465, Nov. 15, 2007.

European Search Report, European Patent Application No. 12166172.2, dated Sep. 26, 2012, 6 Pages.

Sodem Systems, The Sodem Aseptic Battery Transfer Kit, 2000, 3 Pages, Manufacturing & International Distribution: Sodem Systems, Geneva Switzerland.

Van Meer et al., A Disposable Plastic Compact Wrist for Smart Minimally Invasive Surgical Tools, LAAS/CNRS, Aug. 2005.

European Search Report, European Patent Application No. 14184821.8, dated Feb. 12, 2015, 7 pages.

European Search Report, European Patent Application No. 14184806.9, dated Feb. 12, 2015, 7 pages.

International Search Report, PCT/US2014/054756, dated Feb. 12, 2015, 6 pages.

International Search Report, PCT/US2014/054762, dated Feb. 18, 2015, 6 pages.

\* cited by examiner

SURGICAL CLIP HAVING COMPLIANT PORTION

CROSS-REFERENCE TO RELATED APPLICATIONS

This is application is a continuation of U.S. patent application Ser. No. 15/483,419, entitled "Surgical Clip Having Compliant Portion," filed Apr. 10, 2017, which is a continuation of U.S. patent application Ser. No. 15/045,284, entitled "Surgical Clip Having Compliant Portion," filed on Feb. 17, 2016, which is a continuation of U.S. patent application Ser. No. 14/025,904, entitled "Surgical Clip Having Compliant Portion," filed on Sep. 13, 2013, the contents of which are hereby incorporated by reference herein in their entirety.

FIELD OF THE INVENTION

The present invention relates to surgical instruments and in particular to surgical clips and methods used for ligating vessels, other ducts, and the like.

BACKGROUND OF THE INVENTION

During many surgical procedures, the surgeon will have to close or ligate various blood vessels and other ducts before severing them in order to prevent excessive bleeding, and reduce the risk of other complications to the patient. One ligation technique is to tie a suture about the vessel to close the vessel. Alternatively, a surgeon can place a clip having a pair of legs connected at their proximal ends about the vessel, and urge or squeeze the legs together to close the vessel.

One drawback associated with some current clips used for ligating vessels is that the legs of the clip may tend to separate to some extent following release from a clip applier. This phenomenon is called duck-billing. Duck-billing can result in insufficient ligation of a vessel, thus leading to excessive blood loss and/or unnecessary damage to the vessel. Further, some known ligation clips are often difficult to preload into a clip applier because of resistance between the tissue disposed between the jaws and the gripping features on the clip legs.

Accordingly, there remains a need for an improved surgical instrument and method, and in particular for surgical clips used for ligating blood vessels, other ducts, and the like.

SUMMARY OF THE INVENTION

The present invention provides various methods and devices for ligating tissue, such as vessels, other ducts, and the like. In one aspect, a surgical clip is provided that includes a pair of opposed first and second leg members with a knee portion formed therebetween. While the apex can have a variety of configurations, in one embodiment, the apex can have opposed ends joining the proximal ends of said first and second leg members. Moreover, the apex can include a notch formed on an inner surface thereof.

The clip can have a variety of features that help provide a more secure ligation of the vessel. In one exemplary embodiment, the first and second leg members can include an inner surface having at least one tissue-grasping element formed thereon. The tissue-grasping elements can have a variety of configurations, such as a longitudinal tongue formed on the first leg member, and a longitudinal groove formed on the second leg member. The tongue and groove can be complementary and disposed opposite to each other. Moreover, the tongue and groove can extend along the entire length of the inner surface of each leg member, or a portion thereof. The tissue-grasping elements of the first and second leg members can also include at least one channel oriented at an angle with respect to the longitudinal axis of the first and second leg members.

In another exemplary embodiment, the first and second leg members can include an outer surface having at least one raised portion formed thereon. The raised portion can be a pad disposed on an outer surface of each of the first and second leg members located proximal to a point approximately midway between the apex and the knee portion of each leg member. In one embodiment, the raised area can be approximately one-third of the way between the apex and the knee, and closer to the apex.

In another aspect, a device for ligating tissue is disclosed having first and second leg members, with a knee portion formed therebetween. An apex can join the proximal ends of the first and second leg members, such that the first leg member and the second leg member are opposed from one another. While the apex can have a variety of configurations, in one exemplary embodiment, the apex includes a notch formed in an inner surface thereof.

In another aspect, a surgical clip is disclosed being in the form of a substantially U-shaped member that includes an apex that joins first and second leg members. The apex can further include a notch formed therein. In one exemplary embodiment, the leg members can include at least one tissue-grasping element formed on an inner surface thereof, and a knee portion formed between the proximal and distal ends thereof. Moreover, each leg member can have a width of less than about 0.05 inch, and a yield strength greater than about 28 ksi.

In another exemplary embodiment, the clip can include a raised area disposed on an outer surface of each of the first and second leg members proximal to a point between the apex and the knee portion of each leg member. The raised area can be approximately one-third of the way between the apex and the knee, and closer to the apex.

In another aspect, a device for ligating tissue is provided having first and second opposed leg members with proximal and distal ends, and a knee portion formed between the proximal ends of each of the leg members. An apex having opposed ends joins the proximal and distal ends of the opposed leg members. The leg members further include inner and outer surfaces, the outer surface having at least one raised area on a portion thereof. In one embodiment, the raised area is located approximately one-third of the way between the apex and the knee portion, closer to the apex. In other embodiments, the device can further include at least one tissue-grasping feature formed on the inner surface of the opposed leg members, as well as a notch formed on the inner surface of the apex.

In another aspect, a ligation clip is provided having pair of opposed legs joined together at a proximal end by an apex. The opposed legs each can have a distal end and a knee portion disposed distal of the apex, and a raised area formed on an outer surface of each leg between the apex and the knee. The raised area is effective to share with the knee portions a load applied by a closing force such that the knee portions are subjected to less plastic deformation and retain some elasticity, wherein upon release of the closing force the distal ends of the clip remain in contact with one another.

In another aspect, a ligation clip is provided having a compliant portion on an inner surface of at least one leg. The compliant portion is more easily movable by tissue than the compressed legs of the ligation clip. The compliant portion may be formed of a polymer that is absorbable within a patient's body. The compliant portion can cover the inner surface of only the proximal portion of the leg, the inner surface of only a distal portion of the leg, or it can cover the inner surface of the entire length of the leg from the apex to the distal end. The compliant portion may have raised ribs, varying thickness, and varying compliance. The compliant portion can close gaps caused by clips opening elastically after formation, improve clip security, make effectiveness of the clip less sensitive to form, and compensate for a larger opening caused by the elasticity of clips.

A method for ligating vessels is also provided where a closing force is applied to each leg member such that in a partially closed position the knee portions of each leg member are substantially parallel to one another when the distal ends of each leg member are in contact with one another. As the closing force is continued to be applied to the clip, the raised areas and the knee portions share a load applied by the closing force such that the knee portions are subjected to less plastic deformation and retain some elasticity, wherein upon release of the closing force the distal ends of the clip remain in contact with one another. In another aspect, a method for ligating vessels is provided where, upon release of the closing force, a compliant portion continues to maintain a pressure on tissue within the leg members of the clip.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
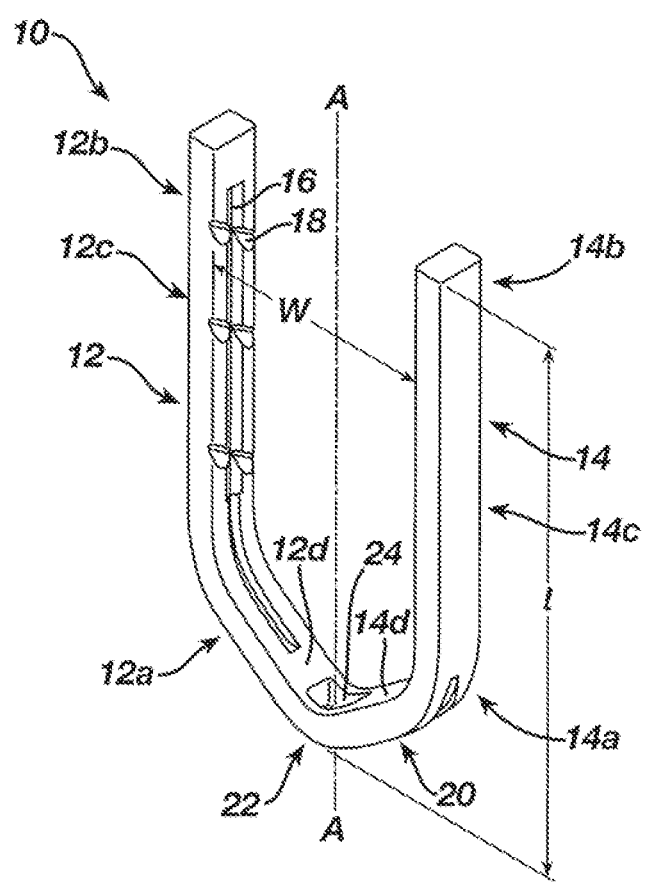
FIG. 1 is a perspective view of one embodiment of a surgical clip disclosed herein.

The present invention provides various devices for ligating tissue, such as vessels, other tubular ducts, and the like. FIGS. 1-4C illustrate exemplary embodiments of a clip disclosed herein in an open position. Referring generally to FIG. 1, the clip 10 in its open position is generally U-shaped having opposed leg members 12, 14 joined at an apex 22. Each leg member 12, 14 has a knee portion 20 disposed distally of the apex 22. Moreover, each leg member 12, 14 has an inner tissue-contacting surface 12*d*, 14*d* and an opposed outer surface 12*c*, 14*c*, both of which may have features to provide a more secure ligation of the vessel or duct. For example, the inner surface(s) 12*d*, 14*d* can include various tissue-grasping elements formed therein (discussed in more detail below). The outer surface(s) 12*c*, 14*c* can have at least one raised area 26 (shown in FIG. 3) formed thereon between the knee portion 20 and the apex 22. While clip 10 is described herein in the context of a device to ligate vessels, one skilled in the art will appreciate that the surgical clip 10 can be used to ligate a variety of other body tissues, including but not limited to, veins, arteries, ducts, or any other tubular member within a patient for which ligation is desired. Moreover, the clip 10 can be used in a variety of clip appliers, thereby effecting a wide range of surgical procedures. Although the clip 10 is described herein with respect to ligation, it is understood that a variety of other applications are possible as well.

The clip 10 can have any shape in its open configuration that allows it to effectively ligate a vessel, such as a substantially U-shaped or a substantially V-shaped design. As noted above, in an exemplary embodiment, the clip 10 is substantially U-shaped. That is, proximal portions 12*a*, 14*a* of the leg members 12, 14 of the clip 10 are oriented at an acute angle with respect to the central axis A of the clip 10, and transition at a knee portion 20, to an orientation where distal portions 12*b*, 14*b* of the leg members 12, 14 are parallel with respect to one another and to central axis A.

One skilled in the art will appreciate that the size of the clip 10 can vary depending upon its particular application. In an exemplary embodiment, the clip 10 can have a length/in the range of about 5 mm to 15 mm, and more preferably in the range of about 7.5 mm to 8.5 mm. In its open configuration, the clip 10 can have a width Was shown in FIG. 3 measured between opposed inner surfaces 12*d*, 14*d* of the leg members 12, 14 in the range of about 2 mm to 8 mm, and more preferably in the range of about 3 mm to 4 mm. The size of the leg members 12, 14 can also vary depending upon the particular application, however in one embodiment, each leg member 12, 14 can have a width w, shown in FIGS. 2D and 2E, less than 0.050 inch, more preferably in the range of about 0.025 inch to about 0.040 inch, most preferably less than about 0.035 inch. Moreover, each leg member 12, 14 can have a height H (shown in FIG. 3) in the range of about 0.015 inch to 0.030 inch, and more preferably in the range of about 0.018 inch to 0.025 inch, and most preferably in the range of about 0.019 inch to 0.020 inch.

The clip can also have physical properties, such as yield strength, that are appropriate for a desired application. In an exemplary embodiment, the yield strength is greater than about 28 ksi and less than about 60 ksi, and more preferably in the range of about 30 ksi to 50 ksi. In general, clip 10 can have a yield strength that is equivalent to or greater than clips having larger dimensions.

Clip 10 is further designed so that, upon closure, a vessel, for example, is completely encased between the leg members 12, 14 of the clip 10. This is done by urging the leg members 12, 14 of the clip 10 together, typically with the assistance of an applier, to surround the vessel.

Referring now to FIGS. 2A-2E, the clip 10 has opposed first and second leg members 12, 14 each having proximal and distal ends 12a, 14a, 12b, 14b. The proximal and distal ends 12a, 14a, 12b, 14b have opposed inner tissue-contacting surfaces 12d, 14d and outer compression-receiving surfaces 12c, 14c that are connected by superior and inferior sides 12e, 14e, 12f, 14f. One skilled in the art will appreciate that the leg members 12, 14 can have any cross-sectional shape that allows them to effectively close and engage tissue, such as a vessel. Exemplary cross-sectional shapes include, but are not limited to, triangular, rectangular, trapezoidal, and pentagonal. As shown, however, the leg members 12, 14 are substantially rectangular. The substantially rectangular leg shape is believed to provide an optimized design that includes a greater bending resistance for a given clip leg space envelope.

The leg members 12, 14 can also have a variety of features formed therein or thereon to assist with the ligation of a vessel or duct. For example, the inner surface 12d, 14d of each leg member 12, 14 can include tissue-grasping elements, and the outer surface 12c, 14c of each leg member 12, 14 can include a knee portion 20 as well as at least one raised area 26. Optionally, one or more grooves may be formed on the outer surface 12c, 14c as well.

As shown in FIGS. 2A-2E, the tissue-grasping elements formed on an inner surface 12d, 14d of each leg member 12, 14 can include both primary 16, 17 and secondary 18 tissue-grasping elements. The primary tissue-grasping elements 16, 17 can have any configuration that allows them to effectively hold a vessel or duct. In one embodiment, the primary tissue-grasping elements can include at least one tongue 17 formed on the inner surface 14d of the second leg member 14 and at least one groove 16 formed on the inner surface 12d the first leg member 12. The groove 16 and tongue 17 can extend continuously along the inner surface 12d, 14d of each leg member 12, 14. Alternatively, the inner surface 12d, 14d can include multiple groove 16 and tongue 17 segments formed therein.

The groove 16 and tongue 17 can be formed in a variety of locations on each of the first and second leg members 12, 14. In one embodiment, the groove 16 and tongue 17 can extend longitudinally along the entire length or along at least a portion of the length of the inner surface 12d, 14d of each respective leg member 12, 14. Alternatively, the groove 16 and tongue 17 can extend from the distal end 12b, 14b of each leg member 12, 14 to just distal from the apex 22, or from the distal end 12b, 14b of each leg member 12, 14 to just distal to the knee portion 20. Moreover, the groove 16 and tongue 17 can extend distally from the apex 22 to a position just distal to the knee portion 20.

Figure 2A:
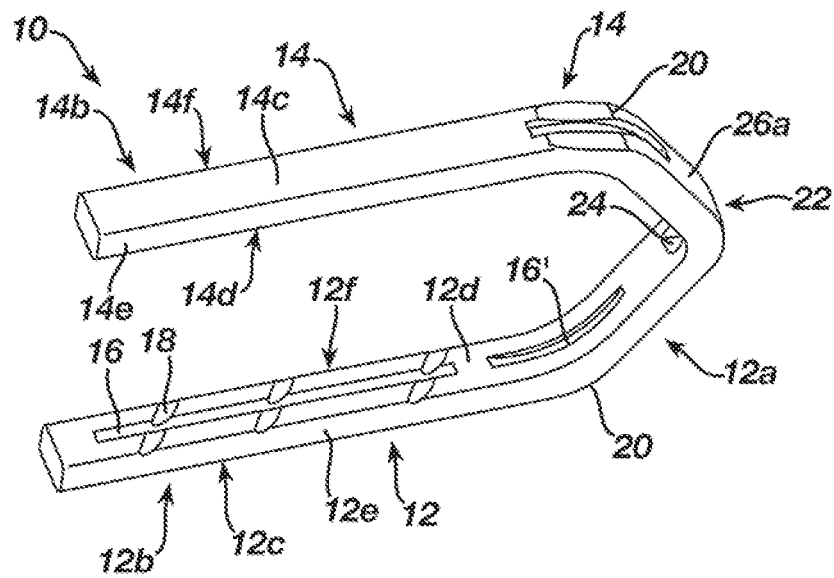
FIG. 2A is a side perspective view of a clip according to another embodiment of the invention.
Figure 4A:
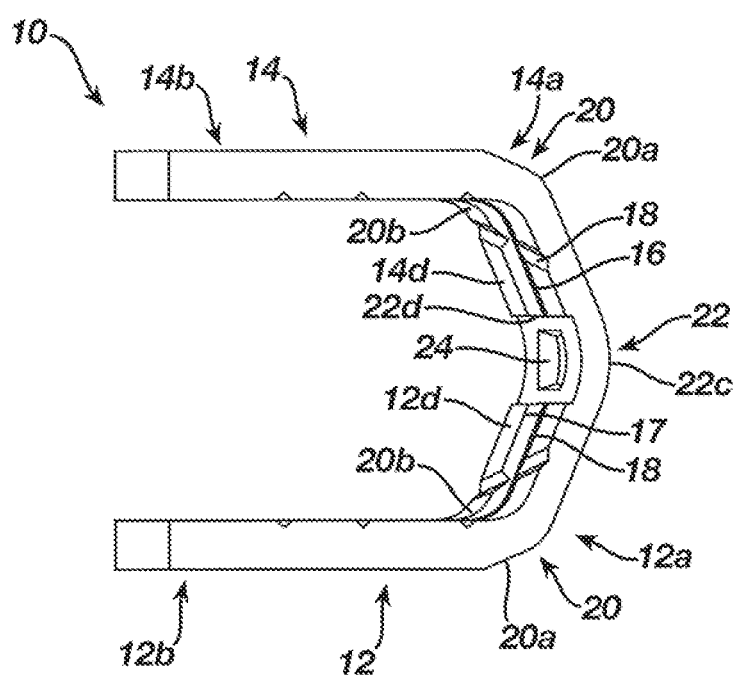
FIG. 4A is a perspective view of a clip.

By way of non-limiting example, FIG. 1 illustrates a longitudinal groove 16 and a longitudinal tongue 17 that extend through the knee portion 20 and terminate just distal to the notch 24 in the apex 22. Alternatively, FIG. 2A illustrates a longitudinal groove 16 and a longitudinal tongue 17 that extend from the distal end 12b, 14b of each leg member 12, 14 to a position just distal to the knee portion 20. A second longitudinal groove 16' and longitudinal tongue 17' combination is then formed just distal to the knee portion 20, extending just distal to the apex 22. Moreover, FIG. 4A illustrates a longitudinal groove 16 and a longitudinal tongue 17 that are formed along the entire inner surface 12d, 14d of each of the first and second leg members 12, 14. The groove 16 and tongue 17 combination shown in FIG. 4A terminates in the notch 24 of the apex 22, as will be discussed in more detail below.

The tongue 17 and groove 16 can be disposed so as to be complementary to one another. Alternatively, the tongue 17 and groove 16 can be located at different locations along each respective leg member 12, 14. In an exemplary embodiment, the tongue 17 are groove 16 are complementary and disposed opposite one another, such that once the clip 10 is applied to a vessel the tongue 17 will urge the tissue of the walls of blood vessel into the corresponding juxtaposed groove 16. This cooperation between the tongue 17 and the groove 16 inhibits longitudinal and angled dislocation of the clip 10 relative to the vessel, and it also effectively reduces the gap between the inner (tissue contacting) surfaces of each respective leg member 12, 14.

Figure 2B:
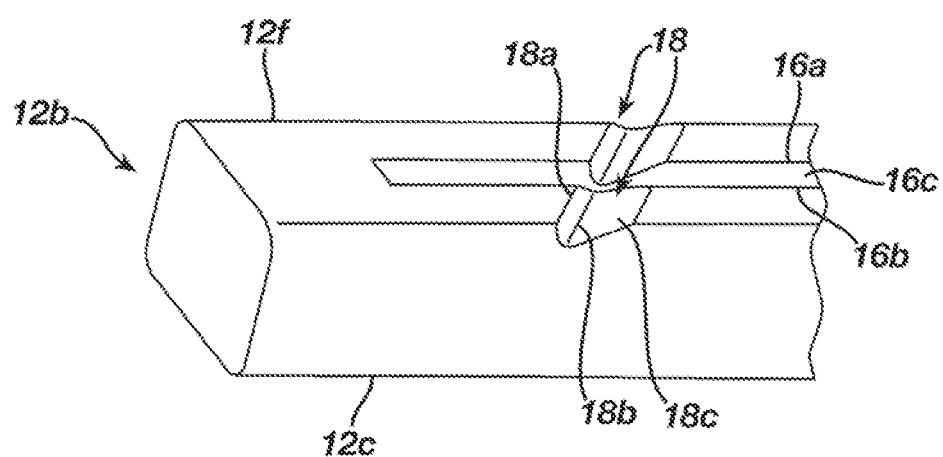
FIG. 2B is a side perspective view of a portion of the distal end of a leg member of the clip of FIG. 2A.
Figure 2C:
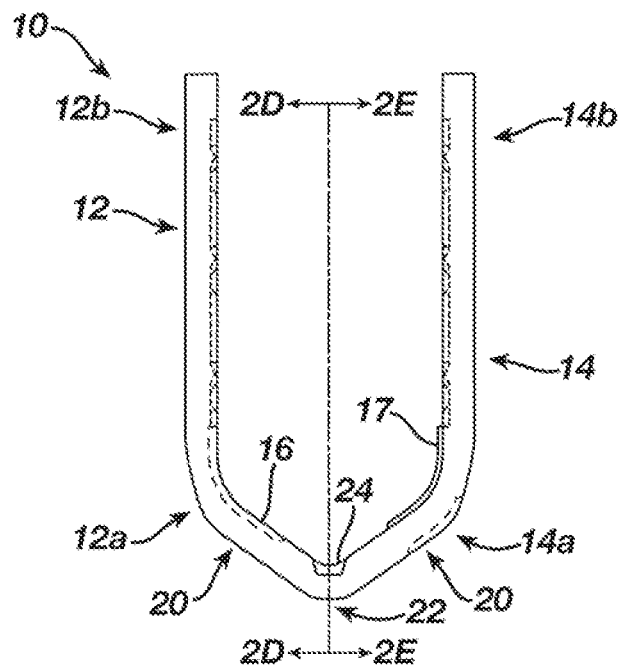
FIG. 2C is a plan view of the clip of FIG. 2A.

One skilled in the art will appreciate that the groove 16 can have a variety of shapes. In an exemplary embodiment, the groove 16 is complementary in shape to the tongue 17 and can be hemispherical, rectangular, triangular, trapezoidal, or oblong. As shown in FIG. 2B, an exemplary embodiment uses a groove 16 that is somewhat triangular, having opposed sidewalls 16a, 16b connected by a base portion 16c. The sidewalls 16a, 16b can be oriented at various angles with respect to the inner surface 12d, 14d of the leg members 12, 14. In one embodiment, the sidewalls 16a, 16b are oriented at an angle less than 120 degrees relative to the inner surface 12d, 14d of the leg members 12, 14, and more preferably at an angle less than 110 degrees relative to the inner surface 12d, 14d of the leg members 12, 14.

One skilled in the art will appreciate that the base portion 16c can have a variety of configurations. For example, the base portion 16c can be planar or slightly rounded. In an exemplary embodiment, however, the base portion 16c is slightly rounded.

One skilled in the art will appreciate that the groove 16 should be of dimensions that are effective to ligate tissue. For example, the groove 16 can have depths in the range of about 0.0015 inch to 0.007 inch, more preferably, in the range of about 0.0025 inch to 0.004 inch. In one exemplary embodiment, the groove 16 can have a depth of about 0.0025 inch. Further, groove 16 can have a width in the range of about 0.004 inch to 0.020 inch, more preferably in the range of about 0.006 inch to 0.013 inch. Moreover, the width of the groove 16 can be uniform throughout the length of the groove 16, or it can decrease in the proximal or distal direction. In an exemplary embodiment, the groove 16 has a uniform width.

One skilled in the art will also appreciate that the tongue 17 can also have a variety of configurations. However, in an exemplary embodiment, the tongue 17 is complementary in shape and size to the groove 16. Thus, the tongue 17 can be hemispherical, rectangular, triangular, trapezoidal, or oblong. In an exemplary embodiment, the tongue 17 is substantially rectangular or trapezoidal.

The tongue 17 can also vary in size, however in an exemplary embodiment, the tongue 17 has a size that is complementary to the size of the groove 16, with a height and a width no greater than, and preferably slightly less than, the dimensions of the groove 16. This provides room for the vessel tissue and minimizes shearing action and locally excessive pressures on the vessel tissue during clip forming. That is, the tongue 17 can have a height in the range of about 0.0015 inch to 0.007 inch, more preferably in the range of about 0.0025 inch to 0.004 inch. In one exemplary embodiment, the tongue 17 can have a height of about 0.0025 inch. The tongue 17 can also have a width in the range of about 0.004 inch to 0.020 inch, more preferably in the range from about 0.006 inch to 0.013 inch. Moreover, and also similar to the groove 16 above, the tongue 17 can have a uniform width or a width that decreases in the proximal or distal direction. In an exemplary embodiment, the tongue 17 has a uniform width.

In addition to primary tissue-grasping elements 16, 17, the inner surfaces 12d, 14d of each of the first and second leg members 12, 14 can have at least one secondary tissue-grasping element 18, as shown in FIG. 2B. While in one embodiment the secondary tissue-grasping elements 18 are formed on the inner surfaces 12d, 14d of both the first and second leg members 12, 14, the secondary tissue-grasping element 18 can optionally be formed on the inner surface 12d, 14d of only one of the first and second leg members 12, 14. One skilled in the art will appreciate that the inner surfaces 12d, 14d of the first and second leg members 12, 14 can have any number of secondary tissue-grasping elements 18. In the exemplary embodiment, the inner surface 12d, 14d has at least four secondary tissue-grasping elements 18.

The secondary tissue-grasping elements 18 can have any configuration that allows them to grasp tissue following application of the clip 10 to the vessel or duct. As shown in FIG. 2B, exemplary secondary tissue-grasping elements 18 are in the form of channels having opposed first and second walls 18a, 18b connected by base wall 18c. The channels are generally saw-toothed in shape, however can also be undercut. In an exemplary embodiment, the first wall 18a is formed at an acute angle relative to the inner surface 12d, 14d of each leg member. In an exemplary embodiment the angle is in the range of about 40 degrees to 90 degrees, and more preferably the angle is about 75 degrees. The second wall 18b is likewise oriented at an acute angle relative to the inner surface 12d, 14d of each leg member. The acute angle of the second wall 18b, which is generally shallower than the angle of the first wall 18a, can be in the range of about 15 degrees to about 75 degrees, and more preferably it is about 45 degrees. One skilled in the art will appreciate that the walls 18a, 18b, 18c can be straight or arcuate, but in the exemplary embodiment the walls 18a, 18b, 18c are slightly arcuate to facilitate grasping.

Figure 2D:
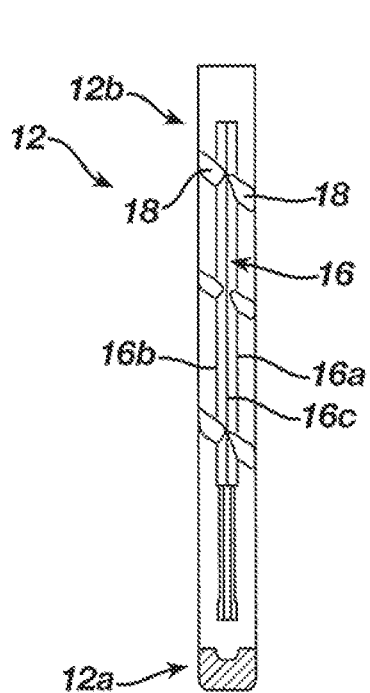
FIG. 2D is a sectional view of the clip of FIG. 2C along the lines 2D-2D.
Figure 2E:
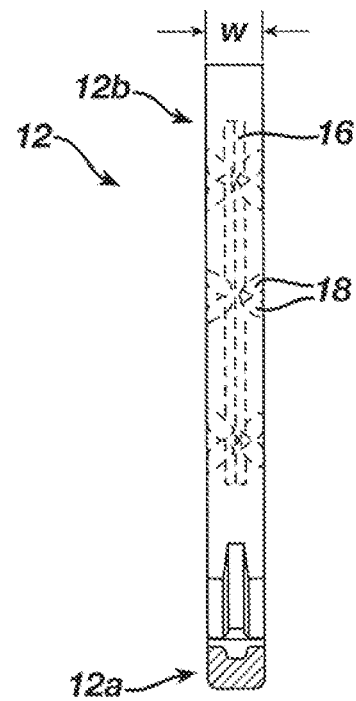
FIG. 2E is a sectional view of the clip of FIG. 2C along lines 2E-2E.

As shown in FIGS. 2D-2E, the secondary tissue-grasping elements 18 extend across the width w of the first and second leg members 12, 14 at an angle (e.g., about 45 degrees) relative to a longitudinal axis of the leg members 12, 14. In an exemplary embodiment, one segment of the secondary tissue-grasping element 18 is located on one side of the tongue 16 or groove 17 on the first leg member 12, and a second segment 18 continues at the same angle on the other side of the tongue 16 or groove 17. The secondary tissue-grasping elements 18 are similarly constructed on the second leg member 14, however they are angled at an orientation opposite that of the first leg member 12. Thus, when the leg members 12, 14 close around a vessel or duct, they form a superimposed "x," as shown in FIG. 2E. This configuration allows for a greater percentage of the tissue to be grasped by the secondary tissue-grasping elements 18, thereby resulting in more effective ligation.

The leg members 12, 14 can have any number of secondary tissue-grasping elements 18 formed thereon. In the exemplary embodiment, however each leg member 12, 14 has three secondary tissue-grasping elements 18 formed thereon. One skilled in the art will appreciate that the secondary tissue-grasping elements 18 can be uniformly or non-uniformly spaced apart from one another. In an exemplary embodiment, the secondary tissue-grasping elements 18 are uniformly spaced apart from one another at a distance in the range of about 0.050 inch to 0.080 inch. Moreover, the secondary tissue-grasping elements 18 can have any size and depth that is effective to engage and maintain contact with tissue. However, in an exemplary embodiment, the secondary tissue-grasping elements 18 are sized in the range of about 0.008 inches to 0.012 inches wide by about 0.0015 inches to 0.0035 inches deep.

One skilled in the art will appreciate that the leg members 12, 14 of the exemplary clip 10, as shown in FIGS. 1-4C, can include any combination of primary tissue-grasping elements 16, 17 and secondary tissue-grasping elements 18. An exemplary clip 10, however, includes both primary and secondary tissue-grasping elements 16, 17, 18. In another exemplary embodiment (not shown), the inner surface 12d, 14d of the leg members 12, 14 can be smooth and free of primary and secondary tissue-grasping elements. The structure and closing properties of the clip 10, as discussed herein, allow adequate tissue ligation without the need for any type of tissue-grasping elements formed on the inner surface 12d, 14d of the leg members 12, 14.

Figure 3:
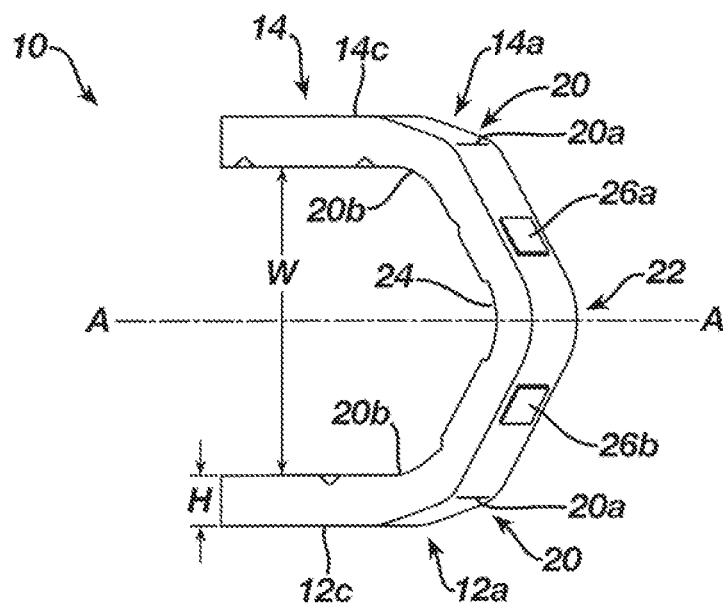
FIG. 3 is another perspective view of a clip.

As shown, for example, in FIG. 3, the outer surface 12c, 14c of each leg member 12, 14 can include a bend or knee portion 20. The knee portion 20 allows the leg members 12, 14 to transition from being acutely angled relative to the central axis A of the clip 10 to being substantially parallel relative to one another and to the central axis A of the clip 10. The angled knee portions 20 of the leg members 12, 14 can be formed at a variety of angles relative to the central axis A of the clip 10, however in an exemplary embodiment the angle can be in the range of about 45 degrees to about 65 degrees. In one embodiment, the knee portion 20 is designed so as to be parallel to the force applying jaws of a clip applier during a part of the clip closing process as shown in FIG. 5B. This construction is believed to enhance clip retention by the clip applier during deployment.

The knee portion 20 can have a variety of configurations to effect the transition of the leg members 12, 14, however an exemplary knee portion 20 has a beveled or flattened outer surface 20a and an arcuate inner surface 20b. The bevel on the outer surface 20a can extend over any length sufficient to effect the transition, however in an exemplary embodiment the bevel is in the range of about 0.030 inch to 0.050 inch. The outer surface 20a of the knee portion 20 can optionally include a groove (not shown) formed therein to facilitate formation of a raised tongue 17 on the inner surface 12d, 14d of the leg members 12, 14. The groove can be similar in shape and size to the longitudinal groove 16, discussed herein with respect to FIGS. 2A-2E. The inner surface 20b of the knee portion 20 can also optionally include features to assist with the ligation of the vessel, duct, or tissue. For example, the inner surface 20b can include primary and/or secondary tissue-grasping elements 16, 17, 18 similar to those discussed above with respect to FIGS. 2B-2D.

As noted above, the outer surface 12c, 14c of each leg member 12, 14 can have features to help provide a more secure occlusion and clip performance. In one embodiment, shown in FIG. 3, a raised area 26 extends over a portion of the width of the leg members 12, 14 that is slightly proximal to the knee portion 20. In an exemplary embodiment, the raised area 26 is located approximately one-third of the way between the apex 22 and the knee portion 20, closer to the apex 22. The raised portion 26 is believed to help to reduce overbending of the knee 20 as well as to help maintain the legs 12, 14 of the clip 10 together after the clip 10 is fully closed. While FIG. 3 shows the raised area 26 formed on both the first and second leg members 12, 14, in alternate embodiments, the raised area 26 can be formed on either the first leg member 12 or the second leg member 14. Moreover, the outer surface 12c, 14c of each leg member 12, 14 can have any number of raised areas 26. In the exemplary embodiment, the outer surface 12c, 14c of each leg member 12, 14 has one raised area 26a, 26b.

The raised area 26a, 26b can have any shape that allows the effective application of compressive force to the apex 22 such that the apex 22 is crimped to a greater degree than the knee portion 20. That is, the raised area 26a, 26b is believed to allow the region of the leg member 12, 14 between the apex 22 and the knee 20 to be more elastic, enabling the knee portion 20 to spring back to a small degree while maintaining adequate contact between the distal ends 12b, 14b of the leg members 12, 14. In an exemplary embodiment, the raised area 26a, 26b is a pad having a shape that is complementary to the shape of the leg member 12, 14. Thus, the raised area 26a, 26b can be triangular, rectangular, trapezoidal, pentagonal, etc., but in an exemplary embodiment, the raised area 26a, 26b is substantially rectangular.

One skilled in the art will appreciate that the raised area 26a, 26b can have a variety of sizes, depending upon whether full closure or partial closure of the clip is desired. By way of non-limiting example, if full closure of the clip is desired, the height of the raised area 26a, 26b should be able to maintain the preload at the distal tips of the leg members 12, 14. In an exemplary embodiment, the raised area 26a, 26b has a height in the range of about 0.0005 inch to 0.0025 inch, and more preferably is about 0.001 inch. The raised area 26a, 26b can also have a length that is large enough so that it can adequately sustain the applied pressure from a clip applier. In an exemplary embodiment, the raised area 26a, 26b can have a length of about 0.020 inch, and a width of about 0.010 inch. If partial closure of the clip is desired, the height of the raised area 26a, 26b can be increased.

Figure 4B:
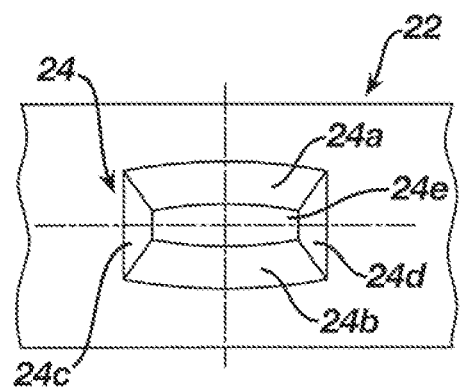
FIG. 4B is a top plan view of an inner portion of the apex of the clip of FIG. 4A.
Figure 4C:
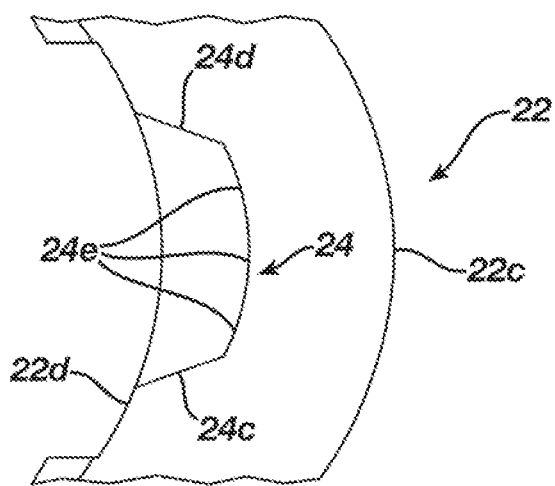
FIG. 4C is a side perspective view of an inner portion of the apex of the clip of FIG. 4A.

As noted above, the proximal ends of each of the leg members 12a, 14a are connected to one another by an apex 22. While the apex 22 can have a variety of shapes, as shown in FIGS. 4A-4C, the apex 22 is substantially U-shaped or substantially V-shaped, and has opposed inner (tissue-contacting) 22d and outer (non-tissue contacting) faces 22c that are connected by superior and inferior surfaces (not shown).

The inner surface 22d of the apex 22 can have a variety of configurations in order to assist with ligation, for example, at least one notch 24 can be formed therein. While the inner surface 22d can have any number of notches formed therein, an exemplary embodiment utilizes one notch 24. One skilled in the art will appreciate that the notch 24 can have any configuration that allows for the ligation of tissue. In an exemplary embodiment, the notch 24 is formed in a U-shaped channel that extends through the inner surface 22d of the apex 22. The U-shaped channel may join the tongue 16 and groove 17 that extend along at least a portion of length of the inner surface 12d, 14d of the leg members 12, 14.

The notch 24 can further have a variety of shapes to optimize its mechanical properties and make it stiff and strong for the amount of material in it, yet leaving open space for the material in compression on the inner side of the clip 10 to flow into during the plastic deformation that occurs during clip formation. In an exemplary embodiment, as shown herein, the notch 24 is substantially trapezoidal. That is, as shown in FIGS. 4B-4C, the notch 24 has opposed first and second walls 24a, 24b connected by opposed third and fourth walls 24c, 24d with a base portion 24e extending therebetween. While the walls 24a, 24b, 24c, 24d can have a variety of configurations, in an exemplary embodiment the walls 24a, 24b, 24c, 24d are formed at an acute angle relative to the inner surface 22d of the apex 22. The angle can be any acute angle, but it is preferably in the range of about 75 degrees. One skilled in the art will appreciate that the walls 24a, 24b, 24c, 24d, 24e can have also have any shape that provides an area into which deformed tissue can flow. As shown, the walls and the base portion 24a, 24b, 24c, 24d, 24e are rounded or slightly contoured.

The notch 24 can have a variety of sizes and depths, perhaps best described in relationship to the thickness and width of the clip leg members 12, 14. The width of notch 24 should be such that the webs of material at apex surface 22d are in the range of about 0.005 inch to 0.010 inch wide. The depth of notch 24 should be in the range of about 30 percent to 60 percent of the distance between apex surfaces 22c and 22d, with an exemplary range of about 30 percent to 40 percent of the distance between surfaces 22c and 22d. The length of notch 24 should be in the range of about 1 times to 2 times the thickness of the clip leg members 12, 14, with an exemplary length in the range of about 1.1 times to 1.4 times the thickness of the clip leg members 12, 14. In the case of larger, wider clips, optimum results might require the use of two or more notches in order to maintain the webs of material at surface 22d in the range of about 0.005 inch to 0.010 inch. Other aspects of multiple notches would be expected to follow the guidelines listed above.

The outer face 22c of the apex 22 can also have a variety of configurations in order to assist with ligation. In an exemplary embodiment, the outer face of the apex 22c has two opposed beveled surfaces that meet in a rounded tip. The outer face 22c of the apex 22 is not sharply formed, but rather has a fabrication-induced radius, thereby allowing for a more secure ligation.

The clip 10 disclosed herein can be made from a variety of surgically-appropriate materials including metals and polymers. Moreover, the material can be a bioabsorbable material or a non-bioabsorbable material. In one embodiment, the clip 10 can be made of a metal or a metal alloy having a relatively high annealed state yield strength and a relatively high strain hardening rate, in comparison to existing ligation clips. Suitable metals include tantalum, titanium, stainless steel, or alloys thereof. By way of non-limiting example, the clip 10 can be made from commercially pure titanium or ASTM grade CP1 titanium. This material, when compared with conventional materials, is able to be strain hardened to a greater extent without causing excessive gaps in the formed clip 10.

Moreover, a small amount of interstitial elements, such as oxygen or nitrogen, can be added to the clip material to maintain the formability of the clip 10. In an exemplary embodiment, oxygen can be incorporated within the clip material. Other interstitial elements can include nitrogen, carbon, and iron. The clip 10 can also optionally be coated with an antimicrobial or antibiotic material in order to increase the effectiveness of the clip against a broad range of infectious agents or pathogens.

Figure 5A:
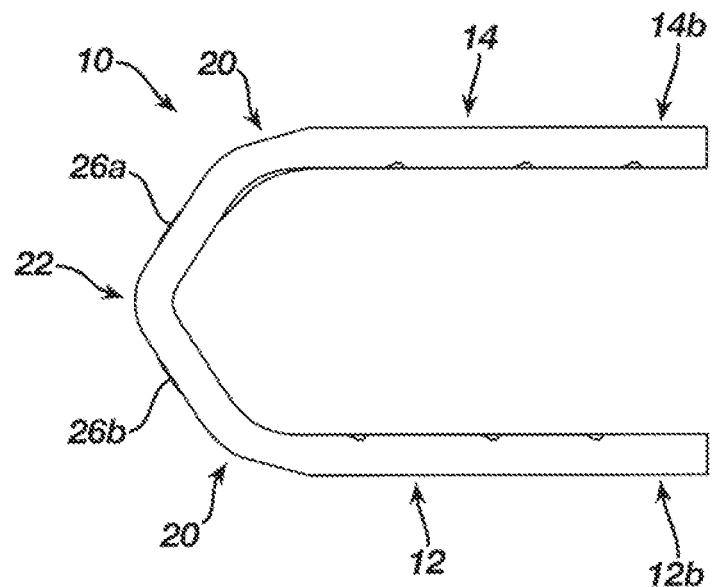
FIG. 5A is another side perspective view of a clip in an open position.
Figure 5B:
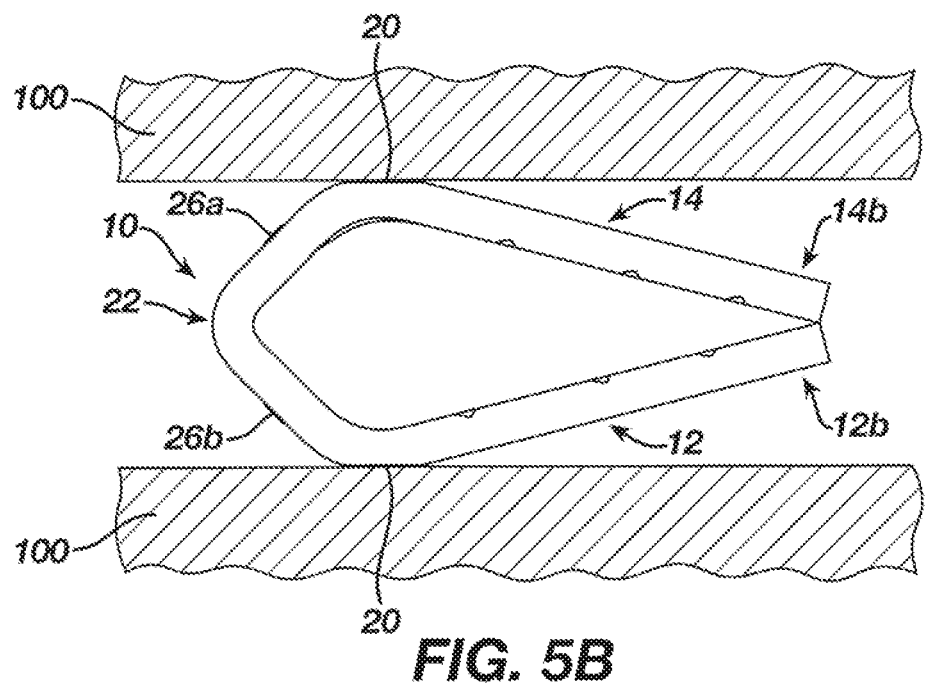
FIG. 5B is a side perspective view of the clip of FIG. 5A in a first state of partial closure.

FIGS. 5A-5E sequentially illustrates selected steps of clip closure, for example to ligate a vessel. As shown in FIG. 5A, an open clip 10 is presented, and it can be placed around a desired vessel. A closing force is then applied to the outer surface 12c, 14c of the leg members 12, 14 by, for example, the force-applying jaws 100 of a clip applier. As clip closure begins, as shown in FIG. 5B, the knee portion 20 and the apex 22 are deformed such that the distal ends 12b, 14b of the leg members 12, 14 are moved inward towards one another. In the position shown in FIG. 5B, the clip features at the knees 20 have become predominately parallel to each other and to the clip applying jaws 100, helping to stabilize the clip 10 in the jaws 100 of the applier.

Figure 5C:
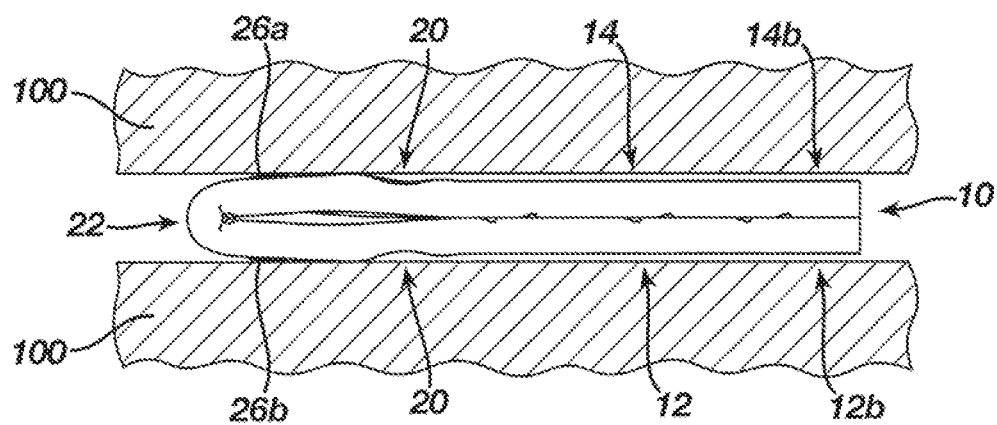
FIG. 5C is a side perspective view of the clip of FIG. 5A in a state of almost full closure.
Figure 5D:
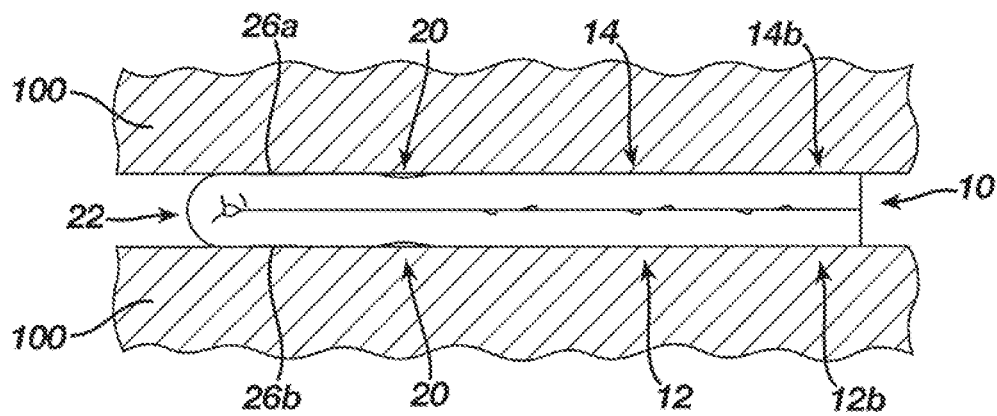
FIG. 5D is a side perspective view of the clip of FIG. 5A fully closed.
Figure 5E:
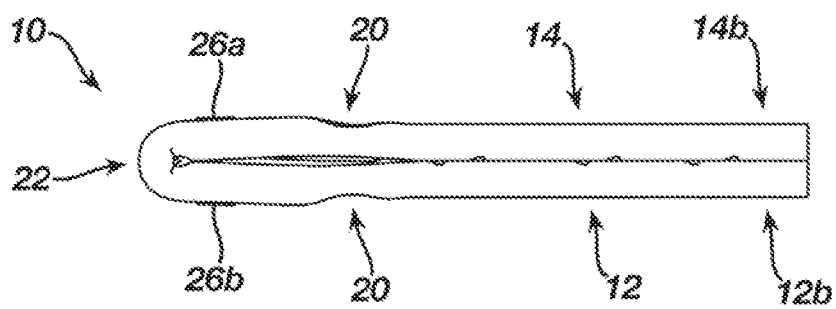
FIG. 5E is a side perspective view of the clip of FIG. 5A following release by a clip applier.

As the application of closing force to the clip 10 continues and the distal ends 12b, 14b of the leg members 12, 14 move closer to one another, the raised area 26 begins to share the clip radial closure forces with the knee portion 20. As a result of this reduction in pressure, the knee 20 is deformed to a lesser extent, as shown in FIG. 5C. FIG. 5D illustrates a condition of full clip closure, with the closing force still applied to the clip 10 by the closing jaws 100. At the final stages of crimping, the raised area 26a, 26b takes some load off of the knee portion 20, thereby reducing the amount of plastic deformation of the knee portion 20. The raised area 26 thus allows the knee portion 20 to have increased elasticity, such that, for example, the knee portion 20 can bend inward slightly when forming loads are released, preloading the tips of the clip 10. This is particularly advantageous in that when the applier is removed from the clip 10 as shown in FIG. 5E, the raised area 26 allows the leg members 12, 14 to remain together from the knee portion 20 to the distal ends 12b, 14b thereof, thereby lessening the duck-billing of the clip 10.

One advantage provided by clip 10 is that it tends to be more resistant to "duck-billing," a condition in which the distal tips of the leg members 12, 14 of the clip 10 tend to separate after the closing force is removed. Some previously known clips tend to duckbill as a result of residual elasticity within the apex. Clip 10 is believed to overcome the tendency to duckbill because the apex 22 is able to crimp to a greater extent and thus minimize the effect of any spring-back. At the same time, increased elasticity between the apex 22 and the knee portion 20 enables any springback at the knee portion 20 to direct the distal ends 12b, 14b of the leg members 12, 14 toward each other. An additional advantage of the above-mentioned characteristics of the clip 10, is that tissue is able to be captured at any location within the clip 10, including near the apex 22 or near the distal ends 12b, 14b of the leg members 12, 14, and still be effectively ligated. As a result, a surgeon can securely ligate vessels having a variety of sizes.

Figure 6:
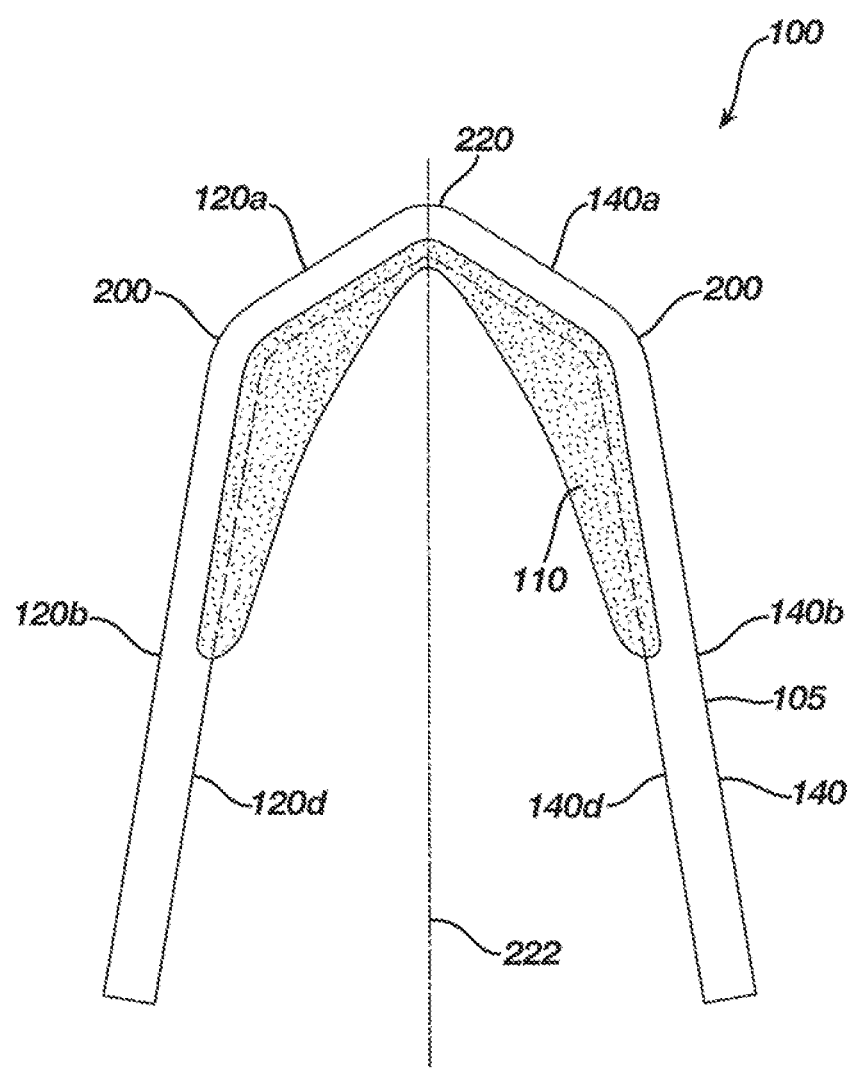
FIG. 6 is a side view of a clip having a compliant element.

FIG. 6 illustrates an exemplary embodiment of a clip 100 having a compliant portion 110. FIG. 6 illustrates clip 100 in the open position. Clip 100 in its open position is generally U-shaped having opposed leg members 120, 140 joined at an apex 220 and arranged about a centerline 222. Each leg member 120, 140 has a knee portion 200 disposed distally of the apex 220. Moreover, each leg member 120, 140 has an inner surface 120d, 140d and an opposed outer surface 120c, 140c. While clip 100 is described herein in the context of a device to ligate vessels, one skilled in the art will appreciate that surgical clip 100 can be used to ligate a variety of other body tissues, including but not limited to, veins, arteries, ducts, or any other tubular member within a patient for which ligation is desired. Moreover, clip 100 can be used in a variety of clip appliers, thereby effecting a wide range of surgical procedures. Although clip 100 is described herein with respect to ligation, it is understood that a variety of other applications are possible as well. Clip 100 may have tissue grasping elements, elasticity-modifying elements, and open volume-creating elements, which create open volume to receive displaced material, as described previously herein.

Clip 100 can have any shape in its open configuration that allows it to effectively ligate a vessel, such as a substantially U-shaped or a substantially V-shaped design. As noted above, in an exemplary embodiment, the clip 100 is substantially U-shaped. That is, proximal portions 120a, 140a of the leg members 120, 140 of the clip 100 are oriented at an acute angle with respect to the central axis A of the clip 100, and transition at a knee portion 200, to an orientation where distal portions 120b, of the leg members 120, 140 are more nearly parallel with respect to one another and to longitudinal centerline 220.

Clip 100 comprises a compliant portion 110 and a rigid portion 105. One or both inner surfaces 120d, 140d may have a compliant portion 110 placed upon them. Compliant portion 110 may extend from apex 220 distally for a portion of the length of leg members 120, 140, as shown in FIG. 6. Alternatively, compliant portion 110 may extend the entire length from apex 220 to the distal ends of leg members 120, 140. Properties and dimensions of compliant portion 110 are chosen to have enough compliance fill gaps left by spring-back of clip 100, but to be less compliant than tissue to be ligated in order to compress the tissue. Properties and dimensions need not be uniform, for example, compliant portion 110 may be stiffer near apex 220 and more compliant, or compressible near the distal ends of leg portions 120, 140. Also, compliance may change as compliant portion 110 is compressed, for example, more compression may cause compliant portion 110 to stiffen. Compliant portion 110 can have properties, such as compressibility, of about four to fifteen psi at 10% to 75% compression. The thickness of compliant portion may be from about 0.01 inch to about 0.05 inch. A designer may use materials and dimensions to cause compliant portion 110 to cooperate with rigid portion 105 to advantageously staunch blood flow within tissue to be ligated.

Compliant portion 110 may be created from biodegradable absorbable polymers that are synthetic or biologic derived. As an example, biodegradable synthetic absorbable polymers can include polydioxanon film sold under the trademark PDS® or with a Polyglycerol sebacate (PGS) film or other biodegradable films from PGA (Polyglycolic acid, marketed under the trade mark Vicryl™), PCL (Polycaprolactone), PLA or PLLA (Polylactic acid), PHA (polyhydroxyalkanoate), PGCL (poliglecaprone 25, sold under the trademark Monocryl), PANACRYL® (Ethicon, Inc., Comperville, N.J.), Polyglactin910, Polyglyconage, PGA/TMC (polyglycolide-trimethylene carbonate sold under the trademark Biosyn®)), polyhydroxybutyrate (PHB), poly(vinylpyrrolidone) (PVP), poly(vinyl alcohol) (PVA), or a blend of copolymerization of the PGA, PCL, PLA, PDS monomers. Suitable biologic derived materials may include but are not limited to platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized cellulose, mussel-based adhesive, poly (amino acid), agarose, polyetheretherketones, amylose, hyaluronan, hyaluronic acid, whey protein, cellulose gum, starch, gelatin, silk, or other material suitable to be mixed with biological material and introduced to a wound or defect site, including combinations of materials, or any material apparent to those of ordinary skill in the art in view of the teachings herein.

Rigid portion 105 of clip 100 can also have physical properties, such as yield strength, that are appropriate for a desired application. In an exemplary embodiment, the yield strength is greater than about 28 ksi and less than about 60 ksi, and more preferably in the range of about 30 ksi to 50 ksi. Rigid portion 105 of clip 100 is generally made of a malleable material that can be formed into a closed shape, but has residual elasticity that causes an amount of springback.

Rigid portion 105 of clip 100 disclosed herein can be made from a variety of surgically-appropriate materials including metals and polymers. Moreover, the material can be a bioabsorbable material or a non-bioabsorbable material. In one embodiment, the clip 100 can be made of a metal or a metal alloy having relatively high annealed state yield strength and a relatively high strain hardening rate, in comparison to existing ligation clips. Suitable metals include tantalum, titanium, stainless steel, or alloys thereof. By way of non-limiting example, the clip 100 can be made from commercially pure titanium or ASTM grade CP1 titanium, CP9 titanium, or CP5 titanium. This material, when compared with conventional materials, is able to be strain hardened to a greater extent without causing excessive gaps in the formed clip 100. Alternatively, the existence of compliant portion 110 allows for materials and geometry that cause more elasticity in rigid portion 105 of clip 100 than would otherwise be considered. Compliant portion 110 will fill gaps caused by elastic springback after clip formation to create a design more forgiving of material variations.

One skilled in the art will appreciate that the size of clip 100 can vary depending upon its particular application. In an exemplary embodiment, clip 100 can have a length/(similar to length/in FIG. 1) in the range of about 5 mm to 15 mm, and more preferably in the range of about 7.5 mm to 8.5 mm. In its open configuration, the clip 100 can have a width W, similar to width W shown in FIG. 3, between opposed inner surfaces 120d, 140d of the leg members 120, 140 in the range of about 2 mm to 8 mm, and more preferably in the range of about 3 mm to 4 mm. The size of the leg members 120, 140 can also vary depending upon the particular application, however in one embodiment, each leg member 120, 140 can have a width w, similar to width w shown in FIG. 2E, less than 0.050 inch, more preferably in the range of about 0.025 inch to about 0.040 inch, most preferably less than about 0.035 inch. Moreover, each leg member 120, 140 can have a height H (similar to height H shown in FIG. 3) in the range of about 0.015 inch to 0.030 inch, and more preferably in the range of about 0.018 inch to 0.025 inch, and most preferably in the range of about 0.019 inch to 0.020 inch.

Clip 100 is further designed so that, upon closure, a vessel, for example, is completely encased between the leg members 120, 140 of the clip 100. This is done by urging the leg members 120, 140 of the clip 100 together, typically with the assistance of an applier, to surround the vessel. A typical applier for clip 100 can be one as described in U.S. Pat. No. 7,731,724 to Huitema et al.

Figure 7:
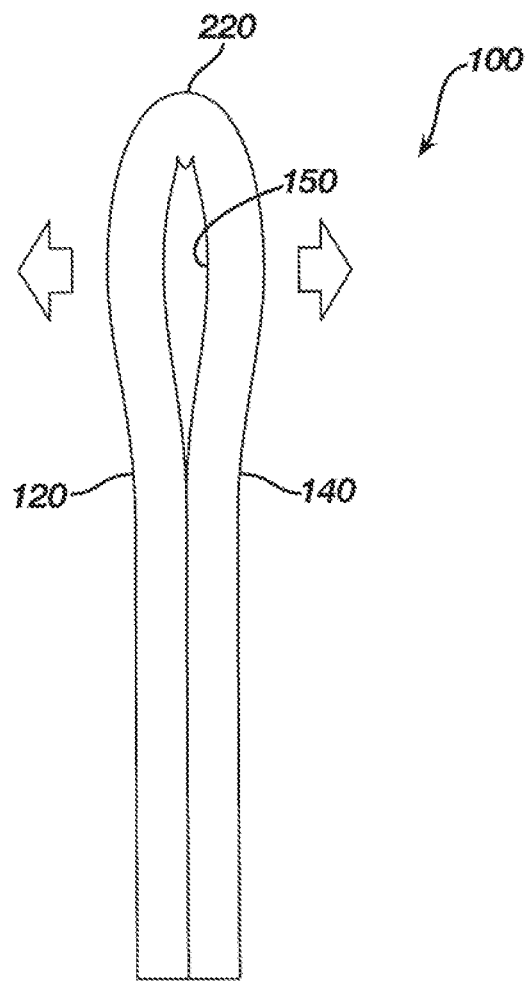
FIG. 7 is a side view of a clip without a compliant element in a state of full closure.

FIG. 7 shows a clip closed only at the distal end leaving a proximal opening 150 between the legs. The material used in rigid portion 105 has elasticity. After clamping the clip closed around tissue, residual elastic forces can cause the proximal portion of the clip to spring back and to open in the directions of the arrows in FIG. 7.

Figure 8:
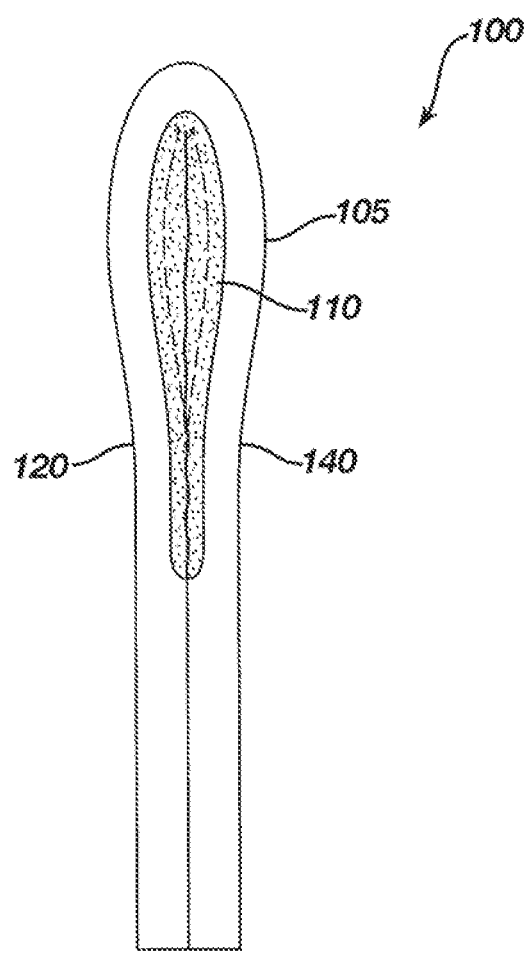
FIG. 8 is a side view of the clip of FIG. 6 in a state of full closure.

FIG. 8 depicts a closed clip 100 showing compliant portion 110 filling proximal opening caused by elasticity in rigid portion 105. Typically, a user would have an applier or forming tool with a clip 100 in the jaws. The user would place clip 100 over tissue to be ligated, such as a blood vessel, and cause the jaws of the applier to move together forcing leg members 120, 140 to move or deform towards each other. The deformation of clip 100 has a plastic component and an elastic component. The user of the applier continues to force leg members 120, 140 together until ligation of tissue is achieved and clip 100 is in the formed position. After formation of clip 100, release of the forming tool can cause leg members 120, 140 of rigid portion 105 to elastically move laterally, or spring back, causing separation of leg members 120, 140. The residual forces from the elastic portion of the deformation cause the leg members 120, 140 to separate the amount of elastic deformation, resulting in an opening 150. However, compliant portion 110 has enough thickness to fill any opening created when leg members 120, 140 separate. Clip 100 can be designed so that the thickness of compliant portion 110 is greater than the gap created by separation after clip formation, or so that the separation amount is less than the total of the thickness of tissue to be ligated and the thickness of compliant portion 110. Clip 100 can further be designed so that force placed upon a vessel by compliant portion 110 is sufficient to keep the vessel closed against the vessel's internal pressure, caused by, for example, blood attempting to flow through a ligated vein or artery. Also, compliant portion 110 may be designed to minimize forces against leg members 120, 140, to minimize separation after clip formation.

Figure 9:
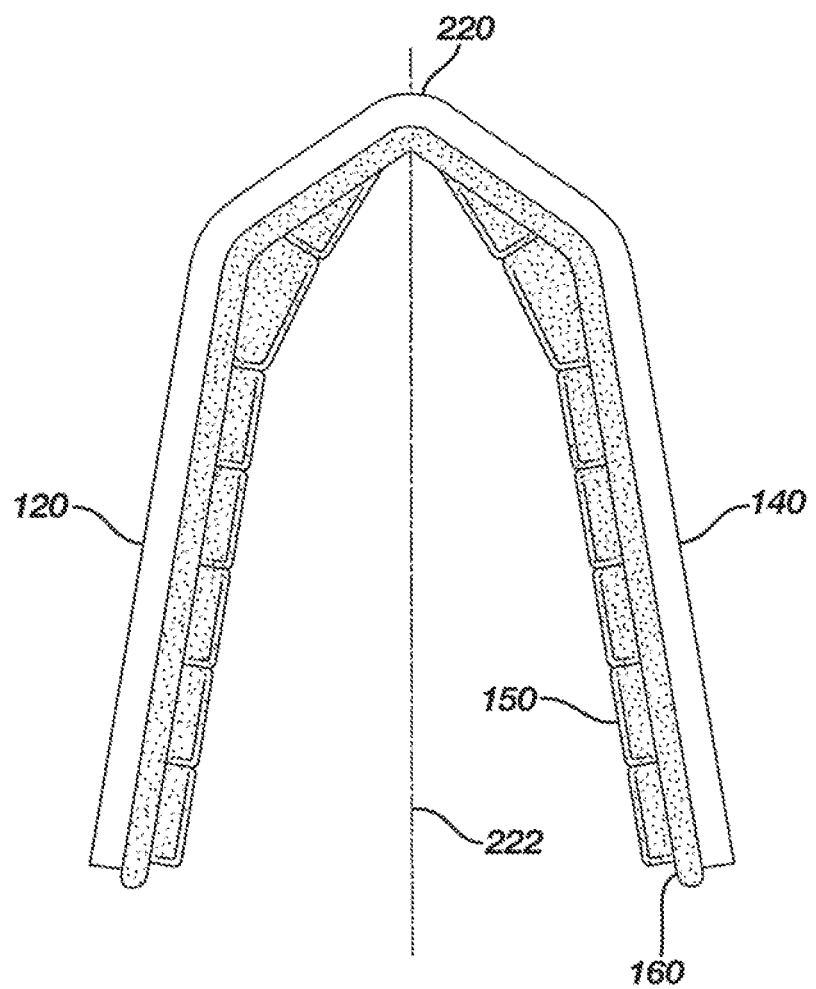
FIG. 9 is a side view of a clip having a compliant element comprising a plurality of ribs.

FIG. 9 shows compliant portion 110 having a plurality of ribs 150. Ribs 150 extend towards longitudinal centerline 222 from a compliant portion base 160 formed along at least one inner surface of inner surfaces 120d and 140d of rigid portion 105. Clip 100 may have a compliant portion 110 with at least one, and perhaps a plurality of ribs 150 extending from a base 160. Ribs 150 may be complementary in shape to each other to interlace upon closing, thus providing greater closure and gripping of tissue placed within leg members 120 of clip 100.

Figure 10:
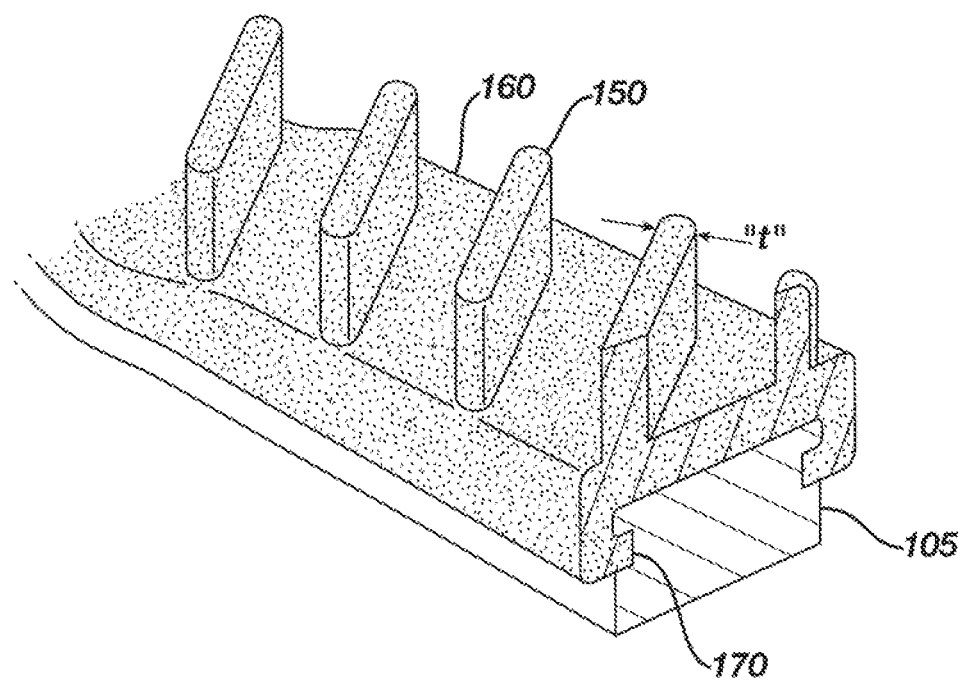
FIG. 10 is a perspective view of a distal end of one leg of a clip having a ribbed compliant element.

FIG. 10 shows in isometric view a set of ribs 150 that are angled to the longitudinal length of leg member 120, and that extend towards longitudinal centerline 222. Ribs 150 may be angled, parallel, or perpendicular to the longitudinal length of leg members 120, 140. Angling ribs 150 at different angles may serve to present different cross-sectional areas to tissue to apply optimum pressure to compliant portion 110 to cause optimum compression. Ribs 150 of FIG. 10 are shown having a constant thickness "t" from base 160 to the open ends of ribs 150. Thickness "t" can vary, however, from a thicker portion near base 160 to a thinner portion at the open end. Thickness "t" could also vary from a thinner dimension near base 160, becoming thicker near the open end, or other variations may occur to a designer of ribs 150.

FIG. 10 further shows in isometric view a groove 170 placed along leg members 120, 140. A portion of one leg member is shown, but groove 170 could be placed along one or both leg members 120, 140. Such a groove 170 can hold compliant portion 110 to rigid portion 105. Compliant portion 110 may be overmolded to rigid portion 105, for example, with the polymer flowing into groove 170 and hardening to hold compliant portion 110 to rigid portion 105. Groove 170 may be substantially rectangular, as shown, or it may be wider at the base to create a dovetail joint to more firmly hold compliant portion 110 to rigid portion 105 of leg members 120, 140.

Figure 11:
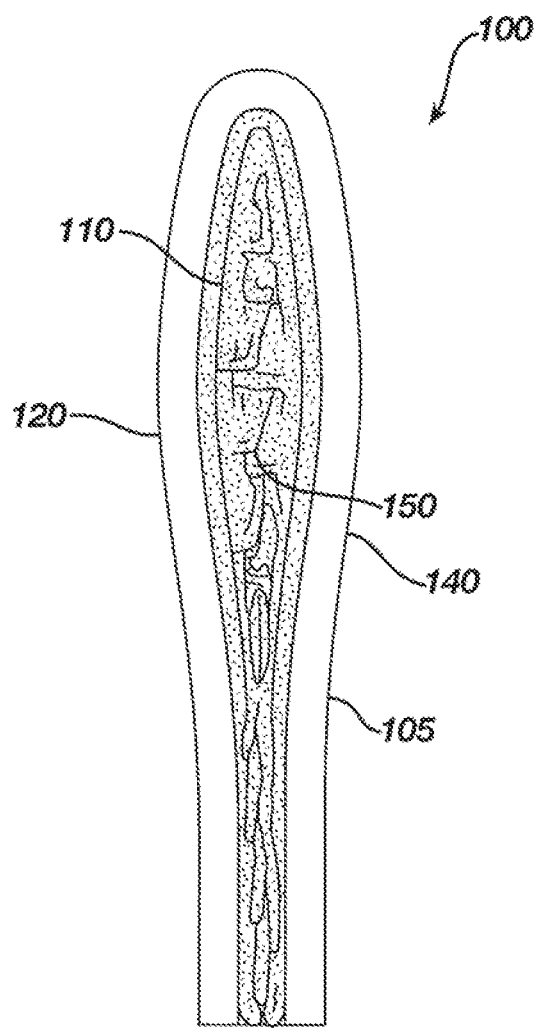
FIG. 11 is a side view of a clip having a ribbed compliant element in a state of full closure.

FIG. 11 shows clip 100 in the closed position, with a ribbed compliant portion 110. When clip 100 is in a closed position, ribs 150 can overlap and interlock to better grip and hold tissue between leg members 120 of clip 100. As another example, some ribs 150 may interlock, however, some ribs 150 may interfere upon closure of clip 100 to cause a desired pressure distribution on tissue to be ligated.

One skilled in the art will appreciate that features presented herein may be used advantageously to optimize holding and tissue compression of surgical clips. Thus, a compliant portion with or without ribs may be used with a clip having, for example, a raised portion, such as a raised portion 26a or 26b (FIG. 3) on an outside portion of one or more leg members 120. Additionally, clip 100 could have tissue contacting surfaces either on compliant portion 110 or rigid portion 105. Clip 100 could have a notch 24, such as notch 24 depicted in FIG. 4A, or tongue and groove configurations as depicted in FIG. 2B.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip, comprising:
   a rigid portion comprising a pair of opposed first and second leg members having proximal and distal ends with a knee portion formed therebetween, the first and second leg members having an inner surface, an outer surface, and first and second side surfaces therebetween connecting the inner and outer surfaces;
   an apex having opposed ends joining the proximal ends of the first and second leg members; and
   an absorbable polymer compliant portion configured to fill a proximal opening defined between the apex and the first and second leg members and be compressed between the first and second leg members distal to the proximal opening when the surgical clip is closed, wherein the absorbable polymer compliant portion comprises a compliant base and a plurality of ribs or ridges interconnected to the compliant base made of a different material than the compliant base and having a different compliance than the compliant base, wherein the compliant base is formed on the inner surface and at least a portion of each of the first and second side surfaces of at least one of the first and second leg members.

2. The surgical clip of claim 1, wherein the compliant base is further formed on at least a portion of the apex and extends distally from the apex beyond at least each knee portion of the first and second leg members.

3. The surgical clip of claim 2, wherein the absorbable polymer compliant portion is thicker on at least a portion of one of the first and second leg members to which the absorbable polymer compliant portion is formed than on the apex to which the absorbable polymer compliant portion is formed.

4. The surgical clip of claim 1, wherein the compliant base portion is elastic and comprises a biodegradable absorbable polymer, and wherein the biodegradable absorbable polymer comprises at least one of the following: polyglycolic acid (PGA), polycaprolactone (PCL), polylactic acid (PLA), polyglycolide-trimethylene carbonate (PGA/TMC), or a copolymer or blend of one or more of PGA, PCL, PLA, PGA/TMC.

5. The surgical clip of claim 1, wherein the plurality of ribs extend away from the inner surface towards the longitudinal centerline.

6. The surgical clip of claim 1, wherein the plurality of ribs extend from the first and second leg members, and wherein a first portion of the plurality of ribs is configured to interlock with each other and a second portion of the plurality of ribs is configured to deform to grip and hold tissue between the first and second leg members in the deformed clip.

7. The surgical clip of claim 1, wherein the proximal opening has a varying width.

8. The surgical clip of claim 1, wherein the absorbable polymer compliant portion is configured to be less compliant than tissue to which the surgical clip is applied.

9. The surgical clip of claim 1, wherein at least one of the first and second leg members comprises a groove extending along a portion of at least one of the first and second side surfaces and the absorbable polymer compliant portion is overmolded onto at least one of the first and second side surfaces of at least one of the first and second leg members via the groove.

10. The surgical clip of claim 1, wherein the absorbable polymer compliant portion is configured to swell in a presence of moisture.

11. The surgical clip of claim 1, wherein the absorbable polymer compliant portion has a compliance that varies with the amount of compression undergone by the absorbable polymer compliant portion.

12. The surgical clip of claim 1, wherein the absorbable polymer compliant portion has a compliance that varies along a longitudinal length of the one of first and second leg members upon which the absorbable polymer compliant portion is formed.

13. A surgical clip, comprising:
   a rigid portion comprising a pair of opposed first and second leg members having proximal and distal ends with a knee portion formed therebetween, the first and second leg members having an inner surface, an outer surface, and first and second side surfaces therebetween connecting the inner and outer surfaces;
   an apex having opposed ends joining the proximal ends of the first and second leg members; and
   an absorbable polymer compliant portion configured to fill a proximal opening defined between the apex and the first and second leg members and be compressed between the first and second leg members distal to the proximal opening when the surgical clip is closed, wherein the absorbable polymer compliant portion comprises a compliant base and a plurality of ribs or ridges interconnected to the compliant base made of a different material than the compliant base and having a different compliance than the compliant base, wherein the compliant base is formed on the inner surface and at least a portion of each of the first and second side surfaces of at least one of the first and second leg members, wherein the compliant base is further formed on at least a portion of the apex and extends distally from the apex beyond at least each knee portion of the first and second leg members, and wherein the compliant base portion is elastic and comprises a biodegradable absorbable polymer, the biodegradable absorbable polymer comprising at least one of the following: polyglycolic acid (PGA), polycaprolactone (PCL), polylactic acid (PLA), polyglycolide-trimethylene carbonate (PGA/TMC), or a copolymer or blend of one or more of PGA, PCL, PLA, PGA/TMC.

* * * * *